United States Patent [19]

Malabarba et al.

[11] Patent Number: 5,500,410
[45] Date of Patent: Mar. 19, 1996

[54] SUBSTITUTED ALKYLAMIDE DERIVATIVES OF TEICOPLANIN

[75] Inventors: Adriano Malabarba, Binasco; Pierfausto Seneci, Brescia; Jürgen K. Kettenring, Varese; Romeo Ciabatti, Novate Milanese, all of Italy

[73] Assignee: Gruppo Lepetit S.p.A., Gerenzano, Italy

[21] Appl. No.: 461,208

[22] Filed: Jun. 5, 1995

Related U.S. Application Data

[63] Continuation of Ser. No. 263,160, Jun. 20, 1994, abandoned, which is a continuation of Ser. No. 761,806, filed as PCT/EP90/00400, Mar. 13, 1990, abandoned.

[30] Foreign Application Priority Data

Mar. 29, 1989 [EP] European Pat. Off. ............. 89105525

[51] Int. Cl.$^6$ .................. A61K 38/08; A61K 38/12; A61K 38/14; C07K 9/00
[52] U.S. Cl. .................. 514/8; 514/9; 530/317; 530/322
[58] Field of Search .................. 530/317, 322; 514/8, 9

[56] References Cited

U.S. PATENT DOCUMENTS

| | | | |
|---|---|---|---|
| 4,239,751 | 12/1980 | Coronelli et al. | 424/118 |
| 4,604,239 | 8/1986 | Michel et al. | 530/317 |
| 4,629,781 | 12/1986 | Strazzolini et al. | 530/317 |
| 4,645,827 | 2/1987 | Malabarba et al. | 530/322 |
| 4,698,418 | 10/1987 | Malabarba et al. | 530/317 |
| 4,954,483 | 9/1990 | Malabarba et al. | 514/9 |
| 5,064,811 | 11/1991 | Borghi et al. | 514/8 |

FOREIGN PATENT DOCUMENTS

| | | |
|---|---|---|
| 0218099 | 4/1987 | European Pat. Off. . |
| 8806600 | 9/1988 | WIPO . |

OTHER PUBLICATIONS

*Chemical Abstract*, vol. 109 (1988) p. 129526z.
A. Malabarba et al., *Synthesis and Biological Activity of Some Esters of the N–Acetylglucosaminyl Aglycone and of the Aglycone of Teicoplanin*, J. of Antibiotics, vol. 40, No. 11, pp. 1572–1587, Nov. 1987.
*Deaminoteicoplanin and Its Derivatives. Synthesis, Antibacterial Activity, and Binding Strength to AC–D–Ala–D–Ala*, Aldo Trani, et al., J. Med Chem. 1989, 32, pp. 310–314.

*Primary Examiner*—Christina Y. Chan
*Attorney, Agent, or Firm*—J. Michael Dixon

[57] ABSTRACT

The present invention is directed to new $C^{63}$ amide derivatives of teicoplanin wherein the amide moiety is derived from a di- or poly-alkylamine, and to a process for preparing them. The derivatives are prepared by reacting a teicoplanin-like product with an active ester forming reagent such as chloroacetonitrile and then contacting said active ester with the appropriate di- or poly-alkylamine. The amide derivatives of the invention are active against gram positive and gram negative bacteria.

19 Claims, No Drawings

SUBSTITUTED ALKYLAMIDE DERIVATIVES OF TEICOPLANIN

This is a continuation of application Ser. No. 08/263,160, filed Jun. 20, 1994, now abandoned, which is a continuation of application Ser. No. 07/761,806, filed as PCT/EP90/00400, Mar. 13, 1990, now abandoned, herein incorporated by reference.

The present invention is directed to substituted alkylamides of teicoplanin compounds having the following formula I SEQ ID No. 1:

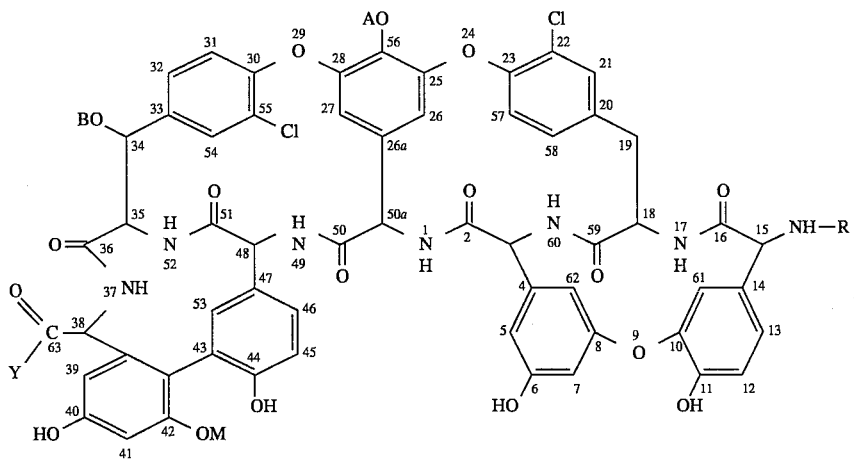

wherein

R represents hydrogen or a protecting group of the amine function;

Y represents a compound of formula

—$NR_1$—$alk_1$—[X—$alk_2$]$_p$—[T—$alk_3$]$_q$—W wherein $R_1$ represents hydrogen or ($C_1$–$C_4$)alkyl;

$alk_1$, $alk_2$ and $alk_3$ each independently represents a linear or branched alkylene of 2 to 10 carbon atoms;

p represents an integer comprised between 1 and 50;

q represents an integer comprised between 0 and 12;

X represents a —$NR_2$— group or an oxygen atom wherein $R_2$ represents hydrogen, ($C_1$–$C_4$)alkyl, a group $alk_4NR_3R_4$ wherein $alk_4$ represents a linear or branched alkylene of 2 to 4 atoms, $R_3$ is hydrogen or ($C_1$–$C_4$)alkyl and $R_4$ is hydrogen, ($C_1$–$C_4$)alkyl or a 5–6 membered cycloalkyl; or $R_1$ and $R_2$ taken together represent a ($C_2$–$C_4$)alkylene moiety connecting the two nitrogen atoms with the proviso that in such case p is 1;

T represents a —$NR_5$— group or an oxygen atom wherein $R_5$ is hydrogen, ($C_1$–$C_4$)alkyl; a group $alk_5NR_6R_7$ wherein $alk_5$ represents a linear or branched alkylene of 2 to 4 atoms, $R_6$ is hydrogen or ($C_1$–$C_4$) alkyl and $R_7$ is hydrogen, ($C_1$–$C_4$)alkyl or a 5–6 membered cycloalkyl; or $R_2$ and $R_5$ taken together represent a ($C_2$–$C_4$)alkylene moiety connecting the two nitrogen atoms with the proviso that in such case both p and q are 1;

W represents hydroxy, $NR_8R_9$ wherein $R_8$ is H or ($C_1$–$C_6$)alkyl and $R_9$ is H, ($C_1$–$C_6$)alkyl, a 5–6 membered cycloalkyl, $COOR_{10}$ wherein $R_{10}$ represents ($C_1$–$C_6$)acyloxy-($C_1$–$C_4$)alkyl, and the group $N^{\oplus}R_{11}R_{12}R_{13}An^{\ominus}$ wherein $R_{11}$, $R_{12}$ and $R_{13}$ each independently represents ($C_1$–$C_4$)alkyl and $An^{\ominus}$ is an anion derived from a pharmaceutically acceptable acid; with the proviso that when simultaneously X is $NR_2$, p is 1 and q is zero, then W is different from hydroxy;

A represents H or —N[($C_9$–$C_{12}$)aliphatic acyl]-beta-D-2-deoxy-2-aminoglucopyranosyl, B represents hydrogen or N-acetyl-beta-D-2-deoxy-2-aminoglucopyranosyl;

I

M represents hydrogen or alpha-D-mannopyranosyl and the pharmaceutically addition salts thereof:

with the further proviso that B represents hydrogen only when A and M are simultaneously hydrogen.

Teicoplanin is the international non-proprietary name (INN) of the antibiotic substance formerly named teichomycin which is obtained by cultivating the strain *Actinoplanes teichomyceticus* nov. sp. ATCC 31121 in a culture medium containing assimilable sources of carbon, nitrogen and inorganic salts (see U.S. Pat. No. 4,239,751).

According to the procedure described in the above cited patent an antibiotic complex containing Teichomycin $A_1$, $A_2$ and $A_3$ is recovered from the separated fermentation broth by extraction with a suitable water insoluble organic solvent and precipitation from the extracting solvent according to common procedures. Teichomycin $A_2$, which is the major factor of the isolated antibiotic complex, is then separated from the other factors by means of column chromatography on SEPHADEX®, chromatography medium. British Patent No. 2121401 discloses that antibiotic Teichomycin $A_2$ actually is a mixture of five closely related co-produced main components.

According to recent structural studies it is possible to represent teicoplanin $A_2$ (formerly Teichomycin $A_2$) main components 1, 2, 3, 4 and 5 by the above formula I wherein R is hydrogen, Y is hydroxy, A represents —N[($C_{10}$–$C_{11}$—)aliphatic acyl]-beta-D-2-deoxy-2-amino-glucopyranosyl, B represent N-acetyl-beta-D-2-deoxy-2-amino-glucopyranosyl, M represents alpha-D-mannopyranosyl.

More particularly, in teicoplanin $A_2$ component 1, the [($C_{10}$–$C_{11}$)-aliphatic acyl] substituent represents Z-4-decenoyl, in teicoplanin $A_2$ component 2 represents 8-methylnonanoyl, in teicoplanin $A_2$ component 3 represents decanoyl, in teicoplanin $A_2$ component 4 represents 8-methyldecanoyl, in teicoplanin $A_2$ component 5 represents 9-methyldecanoyl.

European Patent Application Publication No. 306645 describes production of teicoplanin compounds where the aliphatic acid group of the beta-D-2-deoxy-2-amino-glucopyranosyl moiety is a 6-methyl-octanoyl group (compound A or RS3) or a n-nonayl group (compound B or RS4). The compounds RS-3 (compound A) and RS-4 (Compound B) can be obtained by fermentation of *Actinoplanes teichomyceticus* strains. In particular, a strain of *Actinoplanes teichomyceticus* which is characterized with Gruppo Lepetit's internal code No. A-184 has proved to be a suitable producer of the above mentioned teicoplanin-like derivatives. A sample of said strain has been deposited on Jul. 21, 1987 at the ATCC (American Type Culture Collection, 12301 Parklawn Drive, Rockville, Md. 20852 U.S.A.) under the conditions established by the Budapest Treaty on the International Recognition of the Deposit of Microorganisms for the Purposes of Patent Procedure where it has been assigned the following ATCC number 53649.

The above strain identified by the ATCC No. 53649 is an artificial mutant of *Actinoplanes teichomyceticus* 31121, obtained by treatment with N-methyl-N-nitro-N-nitrosoguanidine and selected on the basis of its ability to produce substantial amounts of teicoplanin-like antibiotics different from the five major components of the teicoplanin complex.

Mutant A-184 shows substantially the same morphological and physiological characteristics as the parent strain ATCC 31121 described in U.S. Pat. No. 4,239,751.

It has now been found that small amounts of RS-3 and RS-4 may be produced also by the parent strain *Actinoplanes teichomyceticus* ATCC 31121 under proper fermentation conditions, but the isolation of the small quantity of RS3 and RS4 from the much larger amounts of the major components of teicoplanin complex produced by said microorganism is very laborious and is not practical for obtaining the desired compounds in a scale suitable for experimental purposes and practical utilization.

Also mutant A-184 produces a certain amount of the major components of teicoplanin complex together with the RS-3 and RS-4 compounds, but their relative ratio in the fermentation broth is much lower than that resulting from the parent strain. Therefore, the separation and recovery of the RS-3 and RS-4 compounds from the fermentation broth of mutant A-184 is much simpler and substantial amounts of the RS3 and RS4 teicoplanin-like derivatives can be obtained.

For the production of RS-3 and RS-4, the *Actinoplanes teichomyceticus* producing strain is fermented under aerobic conditions in an aqueous nutrient medium containing assimilable sources of carbon, nitrogen and inorganic salts.

Preferred carbon sources are glucose, mannose, galactose, starch, corn meal and the like. Preferred nitrogen sources are ammonia, nitrates, soybean meal, peptone, meat extract, yeast extract, tryptone, aminoacids, and the like. Among the inorganic salts which can be incorporated in the culture media there are the customary soluble salts capable of yielding sodium, potassium, iron, zinc, cobalt, manganese, magnesium, calcium, ammonium, chloride, iodide, carbonate, sulfate, phosphate, nitrate and the like ions.

Ordinarily, the antibiotic-producing strain is pre-cultured in a shake flask, then the culture is used to inoculate jar fermenters for production of substantial quantities of the antibiotic substances. The medium used for the pre-culture can be the same as that employed for larger fermentations, but other media can also be employed. The producing-strain can be grown at temperatures between 20° and 40° C., preferably between 26° C. and 32° C.

During fermentation, the antibiotic production can be monitored by testing broth or mycelial extract samples for antibiotic activity for instance by bioassays or TLC or HPLC procedures.

Sensitive organisms to the antibiotics of this invention such as *Bacillus subtilis* and *S. aureus* can be used as test organisms. The bioassay is conveniently performed by the agar diffusion method on agar plates. Maximum production of antibiotic activity generally occurs between the second and the fifth day after inoculation.

The recovery of the antibiotic substances from the fermentation broths of the producing microorganism is conducted according to known per se techniques which include extraction with solvents, precipitation by adding non-solvents or by changing the pH of the solution, partition chromatography, reverse-phase partition chromatography, ion-exchange chromoatography, affinity chromatography and the like.

A preferred procedure includes an affinity chromatography on immobilized D-Alanyl-D-Alanine followed by reverse-phase column chromatography.

Immobilized D-Alanyl-D-Alanine matrices suitable for the present recovery process are disclosed in European Patent Application Publication No. 122969. The preferred matrix in the present process is D-Alanyl-D-alanine coupled with a controlled pore cross-linked polydextrane.

The fermentation broth can be subjected to the affinity chromatography directly after filtration or after a preliminary purification procedure. This latter procedure includes making the whole fermentation mass basic, preferably between pH 9 and 11.5, in order to solubilize the antibiotic substance adsorbed on the mycelium and then filtering. The clear filtrate is brought to pH between 7 and 8 and then subjected to affinity chromatography on immobilized S-Alanyl-D-Alanine, either in column or batchwise.

Elution is performed at more basic pH values (preferably between 9.0 and 11.0) by means of an aqueous base. This aqueous base may be ammonia, a volatile amine, an alkali or alkali metal hydroxide or a basic buffered solution optionally in the presence of a polar organic solvent such as a polar water-miscible solvent. Fractions are collected, neutralized with an acid (either organic or inorganic, preferably, formic acid) and examined by HPLC to individuate those fractions which contain workable amounts of RS3 and RS4 (the term "workable amount" is intended to mean that the amount of desired compound(s) contained in the eluted solution together with the major components of the teicoplanin complex is sufficient to permit its isolation in an appreciable quantity with the usual separation and purification techniques). Usually, the eluted fractions which contain at least 2% of one of the desired compounds on the total HPLC area relative to teicoplanin and teicoplanin-like products, are considered to contain a "workable amount" of the desired compound). Under the following analytical HPLC conditions:

Apparatus: Hewlett Packard liquid chromatograph, mod. 1084 B; the UV detector is set at 254 nm. Column: Erbasil C18 5 micrometer, 150×4.6 mm (Carlo Erba)
Mobile phase: A: 0.02M $NaH_2PO_4/CH_3CN$ (95:5)
B: 0.02M $NaH_2PO_4/CH_3CN$ (25:75)
Gradient

| min | % B |
|---|---|
| 0 | 8 |
| 40 | 40 |
| 45 | 55 |
| 48 | 8 |
| 50 | stop |

Flow rate: 1.5 mn/min
Column pressure: 200 atm
Injection volume: 20 microliter
Attenuation: 8
Chart speed: 0.5 cm/min Standard: teicoplanin A2 complex (A. Borghi et al.: The Journal of Antibiotics, Vol. 37, No. 6, pp 615–620, Jun. 1984) dissolved in water to give a solution at the concentration of 1156.5 microgram/ml, the compound wherein the aliphatic acyl group of the beta-D-2-deoxy-2-aminoglucopyranosyl moiety is 6-methyloctanoyl (compound A) has a retention time (RT) value of 19.93 minutes while the compound wherein the aliphatic acyl group of the beta-D-2-deoxy-2-aminoglucopyranosyl moiety is n-nonanoyl (compound B) has an RT value of 20.96 minutes. As a reference, the RT value for TA2-2, under the same operational conditions is 24.71 minutes.

Those fractions which contain workable amounts of the desired compounds (RS3 and RS4) are pooled and concentrated by ultrafiltration and then lyophilized.

The crude product from lyophilization is dissolved in a polar aprotic organic solvent and then submitted in several portions to semi-preparative HPLC using a gradient mixture of a polar aprotic organic solvent and an aqueous ammonium salt as the mobile phase.

Examples of the polar aprotic organic solvent are ($C_1$–$C_4$)alkyl, lower alkyl amides or thio-amides, such as preferably dimethylformamide or diethylformamide.

Examples of ammonia salts are ammonia formate, ammonia acetate, methylammonium formate; ammonia formate being preferred.

In this case, the stationary phase is preferably a silanized silica gel, i.e. a silica gel functionalized with ($C_8$–$C_{22}$) alkyl groups.

A preferred mobile phase is represented by mixtures of 0.02M ammonium formate/acetonitrile 95:5 and 0.02M ammonium formate/acetonitrile 25:75.

From the eluates of each portion submitted to preparative HPLC the fractions containing Compound A and B respectively as the major products (HPLC analysis) are isolated and combined with those of the other portions. For instance, in a typical operation two solutions are obtained, the first of which contains about 80 percent of the 6-methyloctanoyl derivative with minor amounts (about 1.5 percent) of the n-nonanoyl compound while the second one contains about 90 percent of the n-nonanoyl compound with about 6 percent of 6-methyloctanoyl compound.

The two solutions are concentrated under vacuum, ultrafiltered and then lyophilized giving two solid products that are further purified by repeating the semi-preparative HPLC to yield pure RS-3 and RS-4.

In the paper entitled: "Isolation by HPLC and structural determination of minor components of teicoplanin" given by Zanol et al., at the 17th International Symposium on chromatography, Wien, Sep. 25–30, 1988, other two teicoplanin compounds (RS1 and RS2) are described.

Raw extracts, rich in RS-1 and RS-2 were obtained from the mother liquors of the preparation of several batches of teicoplanin obtained under submerged aerobic fermentation conditions from *Actinoplanes teichomyceticus* ATCC 31121. About 500 mg of crude extract were charged in each run on the Jobin Yvon chromatograph, equipped with a column (50 cm, 2 cm I.D.), packed with RP-18 7 um (Merck) and eluted with a mixture of 0.02M monobasic sodium phosphate/acetonitrile 73/27. After evaporation under vacuum of the acetonitrile, the extract was passed through a column of RP-8 and eluted first with water, to eliminate the salt, and then with water/acetonitrile 30/70. A partially purified mixture was thus obtained. RS-1 and RS-2 present in this last mixture were then isolated by preparative HPLC, using the chromatograph mod. 1084 equipped with a RP-18 7 um column (Merck, 25 cm, 1 cm, 1 cm I.D.) and the same phosphate/acetonitrile eluent used in the first step. After a second desalification step, carried out as described above, and the elimination of acetonitrile, the aqueous fractions containing RS-1 and RS-2 were lyophilized.

Said compounds are characterized in that the aliphatic acyl moieties of the beta-D-2-deoxy-2-aminoglucopyranosyl moiety are respectively 10-methyl-undecanoyl (RS1) and dodecanoyl (RS2).

All the sugar moieties, when present, are linked to the teicoplanin nucleus through O-glycosidic bonds.

In addition, it has been found that it is possible to transform teicoplanin, a pure factor thereof or a mixture of any of said factors in any proportion, into unitary antibiotic products by means of selective hydrolysis of one or two sugar moieties. They are named antibiotic L 17054 and antibiotic L 17046 and are described in European Patent No. 119575 and European Patent No. 119574, respectively.

Preferred hydrolysis conditions for the production of antibiotic L 17054 are: 0.5N hydrochloric acid at a temperature between 70° C. and 90° C. and for a time which is generally between 15 and 90 min.

Antibiotic L 17054 is represented by the above formula I wherein Y is hydroxy, R and A represent hydrogen, B represents N-acetyl-beta-D-2-deoxy-2-amino-glucopyranosyl, M represents alpha-D-mannopyranosyl wherein the sugar moieties are linked to the peptidic nucleus through an O-glycosidic bond.

Preferred hydrolysis conditions for the preparation of antibiotic L 17046 are: 1–3N hydrochloric acid, at a temperature between 50° and 90° C. and for a time which is generally between 30 and 60 min.

Antibiotic L 17046 is represented by the above formula I wherein Y is hydroxy, R, A and M represent hydrogen atoms, and B is N-acetyl-beta-D-2-deoxy-2-amino-glucopyranosyl wherein the sugar moiety is linked to the peptidic nucleus through an O-glycosidic bond.

European Patent Application publication No. 301247 describes de-mannosyl teicoplanin derivatives, i.e. compounds of the formula I above wherein A and B are different from hydrogen, M is hydrogen and Y is hydroxy.

The complete selective cleavage of all the sugar moieties of the teicoplanin compounds gives an aglycone molecule which is called antibiotic L 17392, or deglucoteicoplanin, and is represented by the above formula I wherein Y is hydroxy, and R, A, B, and M each individually represents a hydrogen atom. This selective hydrolysis process is described in European patent application publication No. 146053.

A substance having the same structural formula is disclosed in European Patent Application Publication No. 0090578 and is named antibiotic A 41030 factor B.

This substance is obtained by means of a microbiological process which involves the fermentation of the strain *Streptomyces virginiae* NRRL 12525 or *Streptomyces virginiae* NRRL 15156 in a suitable medium, the isolation, purification and separation into its components of antibiotic A 41030, an antibiotic complex of at least seven factors, antibiotic A 41030 factor B, included.

All the above named compounds, i.e. teicoplanin, teicoplanin $A_2$ complex, teicoplanin $A_2$ component 1, teicoplanin $A_2$ component 2, teicoplanin $A_2$ component 3, teicoplanin $A_2$ component 4, teicoplanin $A_2$ component 5, "compound A or RS3", "compound B or RS 4", RS1, RS2, antibiotic L 17054, antibiotic L 17046, antibiotic L 17392, the de-mannosyl teicoplanin derivatives of European Patent Application publication No. 301247, and any mixture thereof in any proportion, are suitable starting materials for the preparation of the substituted alkylamide derivatives of the invention.

In the present specification "teicoplanin compound" or "teicoplanin starting material" is used to indicate any one of the above starting materials, i.e. teicoplanin as obtained according to U.S. Pat. No. 4,239,751, any further purification thereof, teicoplanin $A_2$ complex, a compound of the above formula I wherein R is hydrogen or an N-protecting group, Y is hydroxy, A represents hydrogen or —N[($C_9$–$C_{12}$)aliphatic acyl]-beta-D-2-deoxy-2-aminoglucopyranosyl, B represents hydrogen or N-acetyl-beta-D-2-deoxy-2-aminoglucopyranosyl, M represents hydrogen or alpha-D-mannopyranosyl, with the proviso that B may represent hydrogen only when A and M are simultaneously hydrogen, a salt thereof, or a mixture thereof in any proportion.

As used herein the term "alkyl", either alone or in combination with other substituents, includes both straight or branched hydrocarbon groups; more particularly, "($C_1$–$C_6$)alkyl" represents a straight or branched aliphatic hydrocarbon chain of 1 to 6 carbon atoms such as methyl, ethyl, propyl, 1-methylethyl, butyl, 1-methylpropyl, 1,1-dimethylethyl, pentyl, 1-methylbutyl, 2-methylbutyl, 1-hexyl, 2-hexyl, 3-hexyl, 3,3-dimethyl-1-butyl, 4-methyl-1-pentyl and 3-methyl-1-pentyl; likewise, "($C_1$–$C_4$)alkyl" represents a straight or branched hydrocarbon chain of 1 to 4 carbon atoms such as those alkyl of 1 to 4 carbons exemplified above.

As used herein the terms "$alk_1$", "$alk_2$", "$alk_3$", represent an independent linear or branched alkylene chain of 2 to 10 carbon atoms such as for example:

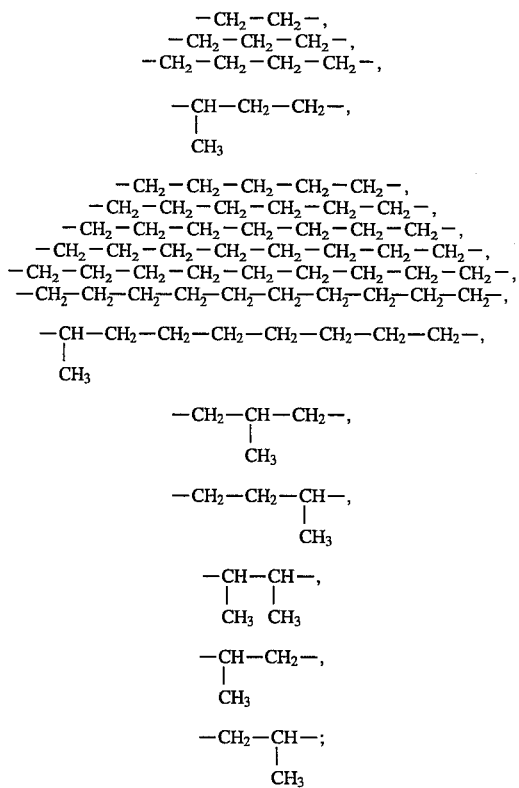

likewise, "$alk_4$" and "$alk_5$" represent an independent linear or branched alkylene chain of 2 to 4 carbon atoms as those alkylene of 2 to 4 carbon atoms exemplified above.

Preferred compounds are those of formula I wherein:

R represents hydrogen or a protecting group of the amine function;

Y represents a compound of formula

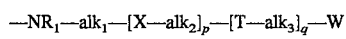

wherein $R_1$ represents hydrogen or ($C_1$–$C_4$)alkyl;

$alk_1$, $alk_2$ and $alk_3$ each independently represents a linear or branched alkylene of 2 to 4 carbon atoms;

P represents an integer comprised between 1 and 12;

q represents an integer comprised between 0 and 12;

X represents a —$NR_2$— group or an oxygen atom wherein $R_2$ represents hydrogen, ($C_1$–$C_4$)alkyl, a group $alk_4NR_3R_4$ wherein $alk_4$ represents a linear or branched alkylene of 2 to 4 atoms, $R_3$ is hydrogen or ($C_1$–$C_4$)alkyl and $R_4$ is hydrogen, ($C_1$–$C_4$)alkyl or a 5–6 membered cycloalkyl; or $R_1$ and $R_2$ taken together represent a ($C_2$–$C_4$)alkylene moiety connecting the two nitrogen atoms with the proviso that in such case p is 1;

T represents a —$NR_5$— group or an oxygen atom wherein $R_5$ is hydrogen, ($C_1$–$C_4$)alkyl a group $alk_5NR_6R_7$ wherein $alk_5$ represents a linear or branched alkylene of 2 to 4 atoms, $R_6$ is hydrogen or ($C_1$–$C_4$)alkyl and $R_7$ is hydrogen, ($C_1$–$C_4$)alkyl or a 5–6 membered cycloalkyl; or $R_2$ and $R_5$ taken together represent a ($C_2$–$C_4$)alkylene moiety-connecting the two nitrogen atoms with the proviso that in such case both p and q are 1;

W represents hydroxy, $NR_8R_9$ wherein $R_8$ is H or ($C_1$–$C_6$)alkyl and $R_9$ is H, ($C_1$–$C_6$)alkyl, a 5–6 membered cycloalkyl, $COOR_{10}$ wherein $R_{10}$ represents ($C_1$–$C_6$)acyloxy-($C_1$–$C_4$)alkyl, and the group $N^{\oplus}R_{11}R_{12}R_{13}An^{\ominus}$ wherein $R_{11}$, $R_{12}$ and $R_{13}$ each independently represents ($C_1$–$C_4$)alkyl and $An^{\ominus}$ is an anion derived from a pharmaceutically acceptable acid; with the proviso that when simultaneously X is $NR_2$, p is 1 and q is zero, then W is different from hydroxy;

A represents H or —N[($C_9$–$C_{12}$) aliphatic acyl]-beta-D-2-deoxy-2-aminoglucopyranosyl, B represents hydrogen or N-acetyl-beta-D-2-deoxy-2-aminoglucopyranosyl;

M represents hydrogen or alpha-D-mannopyranosyl, and the pharmaceutically addition salts thereof;

with the further proviso that B represents hydrogen only when A and M are simultaneously hydrogen.

Preferably, when X and/or T represent —$NR_2$— and/or —$NR_5$— then $alk_4$ and $alk_5$ represent a $C_2$-$C_3$ linear chain.

As described above p is an integer comprised between 1 and 50 and q is an integer comprised between 0 and 12. Preferably, when X and/or T represent —$NR_2$— and/or —$NR_5$— atoms p and q are comprised between 1 and 12, while when both X and T represent oxygen atoms, p and q are such that p+q is comprised between 2 and 50.

The term "$C_5$-$C_6$ cycloalkyl" as used in the specification and claims refers to the cyclopentyl and cyclohexyl group optionally substituted with 1 to 3 lower alkyl such as methyl and ethyl.

Preferred compounds are those of formula I wherein X represents a —$NR_2$— group wherein $R_2$ is hydrogen, a ($C_1$–$C_4$)alkyl or a $alk_4NR_3R_4$.

Another group of preferred compounds are those of formula I wherein p is 1 and X is —$NR_2$— wherein $R_2$ taken together with $R_1$ represent a ($C_2$–$C_3$)alkylene moiety connecting the nitrogen atoms.

In such case are particularly preferred those compounds wherein $alk_1$ represents the group —$CH_2$—$CH_2$—.

A further preferred group of compounds are those of formula I wherein p is 1, q is 1 and X and T are —NR$_2$— and —NR$_5$— respectively, wherein R$_2$ and R$_5$ taken together represent a (C$_2$-C$_3$)alkylene moiety connecting the nitrogen atoms.

In such case are particularly preferred those compounds wherein alk$_2$ represents the group —CH$_2$—CH$_2$—.

Other preferred compounds are represented by formula I wherein X and T are oxygen atoms, p+q is comprised between 2 and 50 and W is hydroxy or NR$_8$R$_9$ wherein R$_8$ is hydrogen or (C$_1$-C$_4$)alkyl and R$_9$ is hydrogen, (C$_1$-C$_4$)alkyl, cyclopentyl or cyclohexyl.

Further preferred compounds are those wherein W represents NR$_8$R$_9$ wherein R$_8$ is as defined and R$_9$ is COOR$_{10}$ being R$_{10}$ a (C$_1$-C$_6$)acyloxy-(C$_1$-C$_4$)alkyl group.

In the term "(C$_1$-C$_6$)acyloxy-(C$_1$-C$_4$)alkyl" the group (C$_1$-C$_4$)alkyl is a methylene moiety optionally substituted with a (C$_1$-C$_3$)linear or branched alkyl chain such as for example:

$$-COOCH_2OCOCH_3,$$

$$-COOCH-OCOCH_3$$
$$\phantom{-COOCH-}|$$
$$\phantom{-COOCH-O}CH_3$$

$$-COOCH-OCOCH_3$$
$$\phantom{-COOCH-}|$$
$$\phantom{-COOCH-}CH_2CH_3$$

and the like.

According to the general definitions given above representative examples of the group:

$$-NR_1-alk_1-[X-alk_2]_p-[T-alk_3]_q-W$$

are the following:

—NH(CH$_2$)$_2$—NH(CH$_2$)$_2$—NH$_2$
—NH(CH$_2$)$_2$—NH(CH$_2$)$_3$—NH$_2$
—NH(CH$_2$)$_2$—NH(CH$_2$)$_4$—NH$_2$
—NH(CH$_2$)$_4$—NH(CH$_2$)$_2$—NH$_2$
—NH(CH$_2$)$_3$—NH(CH$_2$)$_4$—NH$_2$
—NH(CH$_2$)$_2$—NH(CH$_2$)$_3$—NH(CH$_2$)$_2$—NH$_2$
—NH(CH$_2$)$_2$—NH(CH$_2$)$_4$—NH(CH$_2$)$_2$—NH$_2$
—NH(CH$_2$)$_3$—NH(CH$_2$)$_4$—NH(CH$_2$)$_3$—NH$_2$
—NH(CH$_2$)$_2$—NH(CH$_2$)$_3$—NH(CH$_2$)$_4$—NH$_2$
—NH(CH$_2$)$_4$—NH(CH$_2$)$_3$—NH(CH$_2$)$_4$—NH$_2$
—NH(CH$_2$)$_3$NH(CH$_2$)$_9$—NH(CH$_2$)$_3$NH$_2$
—NH(CH$_2$)$_3$NH(CH$_2$)$_{10}$—NH(CH$_2$)$_3$NH$_2$
—NH[(CH$_2$)$_2$NH]$_2$—(CH$_2$)$_2$—NH$_2$
—NH[(CH$_2$)$_3$NH]$_2$—(CH$_2$)$_3$—NH$_2$
—NH[(CH$_2$)$_4$NH]$_5$—(CH$_2$)$_4$—NH$_2$
—NH[(CH$_2$)$_5$NH]$_3$—(CH$_2$)$_5$—NH$_2$

—NH(CH$_2$)$_3$N—(CH$_2$)$_3$N(CH$_3$)$_2$
$\phantom{-NH(CH_2)_3}|$
$\phantom{-NH(CH_2)_3}$(CH$_2$)$_3$NH$_2$ —NH(CH$_2$)$_3$N—(CH$_2$)$_3$N(C$_2$H$_5$)$_2$
$\phantom{-NH(CH_2)_3}|$
$\phantom{-NH(CH_2)_3}$(CH$_2$)$_3$NH$_2$ —NH(CH$_2$)$_2$—NH(CH$_2$)$_2$—NHCH$_3$
—NH(CH$_2$)$_2$—NH(CH$_2$)$_2$—NHC$_2$H$_5$
—NH(CH$_2$)$_2$—NH(CH$_2$)$_4$—NH(nC$_4$H$_9$)

—NH(CH$_2$)$_2$—NH(CH$_2$)$_2$—NH(CH$_2$)$_3$—NH—⟨cyclopentyl⟩

—NH(CH$_2$)$_2$—NH(CH$_2$)$_3$—NH(CH$_2$)$_4$—N—(nC$_4$H$_9$)
$\phantom{-NH(CH_2)_2-NH(CH_2)_3-NH(CH_2)_4-}|$
$\phantom{-NH(CH_2)_2-NH(CH_2)_3-NH(CH_2)_4-}$CH$_3$ -continued —N(CH$_2$)$_2$—NH—(CH$_2$)$_4$—N—⟨cyclohexyl⟩
$\phantom{-N(CH_2)_2-}|\phantom{-NH-(CH_2)_4-}|$
$\phantom{-N(CH_2)_2-}$CH$_3$ $\phantom{-NH-(CH_2)_4-}$CH$_3$

—NH(CH$_2$)$_3$—N[(CH$_2$)$_3$NH$_2$]$_2$

—N(CH$_2$)$_2$—N(CH$_2$)$_2$—N—(CH$_2$)$_3$—N(CH$_3$)$_2$
$\phantom{-N(CH}|\phantom{2-N(CH}|\phantom{2-N-(C}|$
$\phantom{-N(}$CH$_3$ $\phantom{-N(}$CH$_3$ $\phantom{-N}$CH$_3$ —N(CH$_2$)$_2$[N(CH$_2$)]$_2$—N(CH$_3$)$_2$
$\phantom{-N(}$|$\phantom{-N(CH}$|
$\phantom{-N(}$CH$_3$ $\phantom{-N}$CH$_3$ —N(CH$_2$)$_3$—N—(CH$_2$)$_2$—N(CH$_3$)(C$_2$H$_5$)$_2$... 
$\phantom{-N(}$| $\phantom{-N-(}$| $\phantom{-N-(CH}$|
$\phantom{-N(}$C$_2$H$_5$ $\phantom{-N}$C$_2$H$_5$ $\phantom{-N}$C$_2$H$_5$ —N—(CH$_2$)$_3$—N—CH$_2$CH$_2$(O—CH$_2$CH$_2$)$_2$OH
$\phantom{-N}$| $\phantom{-(CH_2)_3-}$|
$\phantom{-N}$CH$_3$ $\phantom{-(CH_2)_3-}$CH$_3$

—NH(CH$_2$)$_3$NH(CH$_2$)$_4$NHCOOCH(CH$_3$)OCOCH$_3$

—NH(CH$_2$)$_2$—N—(CH$_2$)$_2$—NH$_2$
$\phantom{-NH(CH_2)_2-}|$
$\phantom{-NH(CH_2)_2-}$(CH$_2$)$_2$NH$_2$ —NH(CH$_2$)$_3$—N—(CH$_2$)$_3$—NH$_2$
$\phantom{-NH(CH_2)_3-}|$
$\phantom{-NH(CH_2)_3-}$(CH$_2$)$_3$NH$_2$ —N(CH$_2$)$_3$—N(CH$_2$)$_2$—N(CH$_3$)$_3$Cl$^{\ominus}$
$\phantom{-N}$| $\phantom{(CH_2)_3-}$|
$\phantom{-N}$CH$_3$ $\phantom{(CH_2)_3-}$CH$_3$ —NH—(CH$_2$)$_3$—N(CH$_2$)$_3$—NH—⟨cyclopentyl⟩
$\phantom{-NH-(CH_2)_3-}|$
$\phantom{-NH-(CH_2)_3-}$(CH$_2$)$_3$NH—⟨cyclopentyl⟩

—NH(CH$_2$)$_2$—[O(CH$_2$)$_2$]$_2$—O(CH$_2$)$_2$—N(CH$_3$)$_2$

—NH(CH$_2$)$_3$—[O(CH$_2$)$_3$]$_4$—O(CH$_2$)$_4$—N(CH$_3$)(C$_2$H$_5$)

—NH(CH$_2$)$_4$—[O(CH$_2$)$_2$]$_8$—O(CH$_2$)$_2$—NH$_2$

—NH—CH(CH$_3$)CH$_2$—[OCH$_2$CH$_2$]$_{42}$OCH$_2$CH(CH$_3$)NH$_2$

—NHCH—CH$_2$—[O(CH$_2$)$_2$]$_{11}$—OCH$_2$—CH—NH$_2$
$\phantom{-NH}$| $\phantom{CH_2-[O(CH_2)_2]_{11}-OCH_2-}$|
$\phantom{-NH}$CH$_3$ $\phantom{CH_2-[O(CH_2)_2]_{11}-OCH_2-}$CH$_3$ —NH(CH$_2$)$_2$—[O—(CH—CH$_2$)$_2$]$_3$—O(CH$_2$)$_2$—N(CH$_3$)(C$_2$H$_5$)
$\phantom{-NH(CH_2)_2-[O-}$| 
$\phantom{-NH(CH_2)_2-[O-}$CH$_3$

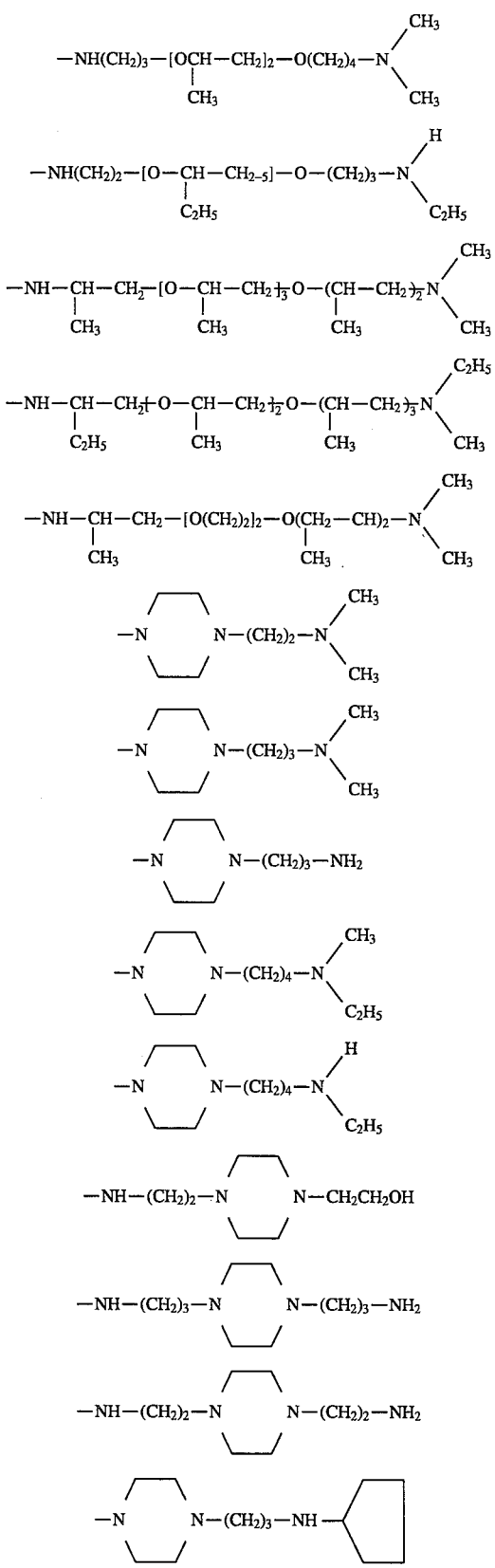

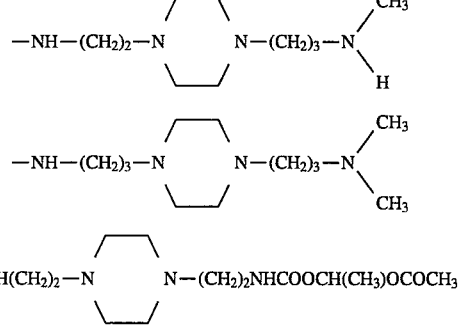

—NH(CH₂)₂—N⟨⟩N—(CH₂)₂NHCOOCH(CH₃)OCOCH₃

The compounds of this invention show antimicrobial activity and are useful as semi-synthetic antibacterial agents against gram positive bacteria but are also particularly active against gram negative bacteria and more particularly against *Escherichia coli* and *Pseudomonas aeruginosa*.

Various $C^{63}$ amide derivatives of teicoplanin complex, single components and the aglycon and pseudoaglycons thereof are described in European patent application publication No. 218099 and International Patent application publication No. WO 88/06600.

The compounds of the present invention are prepared by amidation of the corresponding derivatives of the formula I wherein Y is OH, (i.e. the corresponding carboxy acids).

The substances used as starting materials for the manufacture of the compounds of this invention described above, can be either individual products or mixtures of one or more products.

Since said starting materials for the preparation of the compounds of the present invention can be used in both said forms, the resulting end products may, in turn, be individual compounds or mixtures of two or more compounds of the above formula I. These mixtures of compounds are also part of the invention and may be used as such for their biological applications and uses or may be eventually separated in their individual components by known procedures described in the art. Examples of separation procedures suitable for the purpose of obtaining individual components from end products mixtures of teicoplanin amide derivatives are those described in the following documents: European Patent Applications Publication No. 218099 and International Patent Application Publication No. WO 88/06600.

The amidation procedures described in the two above mentioned European Patent Application and International Patent Application can be used also for the preparation of the compounds of this invention. Said procedures involve condensing the carboxy acid starting materials mentioned above with an excess of the appropriate amine of the formula II:

$$NHR_1—alk_1—[X—alk_2]_p—[T—alk_3]_q—W \qquad II$$

wherein $R_1$, $alk_1$, $alk_2$, $alk_3$, X, T, p, q and W have the same meanings as above, in an inert organic solvent in the presence of a condensing agent.

Inert organic solvents useful for the amidation reaction are those organic aprotic solvents which do not unfavorably interfere with the reaction course and are capable of at least partially solubilizing the teicoplanin starting material.

Examples of said inert organic solvents are organic amides, alkyl ethers, ethers of glycols and polyols, phosphoramides and sulfoxides. Preferred examples of inert organic solvents are: dimethylformamide, dimethoxyethane, hexamethylphosphoramide, dimethylsulfoxide and mixtures thereof.

The condensing agent in the process of the invention is one suitable for forming amide bonds in organic compounds and in particular in peptide synthesis.

Representative examples of condensing agents are ($C_1$–$C_4$)alkyl, phenyl or heterocyclic phosphorazidates such as, diphenyl phosphorazidate, diethyl phosphorazidate, di(4-nitrophenyl)phosphorazidate, dimorpholylphosphorazidate and diphenylphosphorochloridate. The preferred condensing agent is diphenyl phosphorazidate, i.e. phosphoric acid diphenyl ester azide (DPPA). In the amidation process of the invention described here, the amine reactant is normally used in a molar excess.

In general, when the amine reactant is a fairly unexpensive or easily obtainable reactant, a 2- to 6-fold molar excess is used while a 3 to 4-fold molar excess is preferred.

For the amidation to proceed, it is necessary that the amine be capable of forming a salt with the carboxy function of the teicoplanin starting material. In case the amine is not strong enough to form such a salt in the selected reaction medium, it is necessary to add a salt-forming base to the reaction mixture at least in an equimolecular amount with the teicoplanin starting material.

Use of a Low molar excess of the amine reactant with addition of a salt-forming base is a suitable method when the amine reactant is a rather expensive or hardly obtainable product.

Examples of said salt-forming bases are tertiary organic aliphatic or heterocyclic amines such as trimethylamine, triethylamine, N-methyl pyrrolidine or picoline, and the like.

The condensing agent is generally employed in a slight molar excess such as from 1.2 to 1.7 times and preferably 1.5 times the teicoplanin starting compound.

In addition, the amine reactant may also conveniently be introduced in the reaction medium as a corresponding acid addition salt, e.g. the hydrochloride. In this case, at least a double molar proportion and preferably a 2 to 4 fold molar excess of a strong base capable of freeing the amine from its salts, is used. Also in this case, the suitable base is a tertiary organic aliphatic or heterocyclic amine like those exemplified above. In fact, at least in some instances, the use of a salt of the amine which is then freed in situ with the above mentioned bases, is highly preferred, especially when the salt is more stable than the corresponding free amine.

The reaction temperature will vary considerably depending on the specific starting materials and reaction conditions. In general, it is preferred to conduct the reaction at temperatures between 0°–20° C.

Also the reaction time will vary considerably depending on the other reaction parameters. In general, the condensation reaction is completed in about 24–48 h.

In any case, the reaction course is monitored by TLC or preferably by HPLC according to methods known in the art.

On the basis of the results of these assays a man skilled in the art will be able to evaluate the reaction course and decide when to stop the reaction and start working up the reaction mass according to known per se techniques which include, for instance, extraction with solvents, precipitation by addition of non-solvents, etc., in conjunction with further common separation operations and purifications, e.g. by column chromatography.

If the amine reactant contains other functions which are not inert under the selected reaction conditions, said functions are suitably protected by means of per se known protecting groups.

According to a further preferred embodiment of this invention, the compounds of formula I wherein Y is a group as defined above can be prepared by reacting an "activated ester" of the carboxylic acid of the same formula I, wherein Y is OH and the $N^{15}$-amino function is preferably protected, with an appropriate amine of formula II.

The $N^{15}$-amino function can be protected by methods known per se in the art such as those described in reference books like T. W. Greene, "Protective Groups in Organic Synthesis", John Wiley and Sons, New York, 1981, and M. Mc. Omie, "Protecting Groups in Organic Chemistry" Plenum Press, New York, 1973.

The protecting groups must be stable at the conditions of the reaction process, must not unfavorably interfere with the amidation reaction, and must be easily cleavable and removable from the reaction medium at the end of the reaction without altering the newly formed amide bond and the overall structure of the compounds, e.g. sugar components.

Representative examples of N-protecting groups which may be advantageously used in the process of the invention for protecting the $N^{15}$ primary amino function of the teicoplanin starting material and, when appropriate, the amino function of the amine II reactant, are carbamate forming reagents characterized by the following oxycarbonyl groups: 1,1-dimethylpropynyloxycarbonyl, t-butyloxycarbonyl, vinyloxycarbonyl, aryloxycarbonyl, cinnamyloxycarbonyl, benzyloxycarbonyl, p-nitrobenzyloxycarbonyl,3,4-dimethoxy- 6-nitrobenzyloxycarbonyl, 2,4-dichlorobenzyloxycarbonyl, 5-benzisoxazolylmethyloxycarbonyl, 9-anthranylmethyloxycarbonyl, diphenylmethyloxycarbonyl, isonicotinyloxycarbonyl, diphenylmethyloxycarbonyl, isonicotinyloxycarbonyl, S-benzyloxycarbonyl, and the like.

Other suitable N-protecting agents are aldehydes or ketones, or derivatives thereof which are capable of forming Schiff bases with the amino group to be protected.

Preferred examples of such Schiff base forming agents are benzaldehydes and particularly preferred is 2-hydroxybenzaldehyde (salicylaldehyde) .

A convenient mean of protection is, in some instances, the formation of a benzyliden derivative which may be prepared by reacting the amine with benzaldehyde in a lower alkanol, such as ethanol, preferably at room temperature. After the reaction with the selected teicoplanin starting material has been completed, the benzylidene protecting group may be removed as known in the art, e.g. by catalytic hydrogenation, using, for instance, Palladium on carbon as the catalyst.

In this case, however, attention should be paid to the presence of groups which may be modified by catalytic hydrogenation. A typical consequence of the catalytic hydrogenation of an amino-protected derivative of formula I wherein A represents a group as above defined whose acyl portion is (Z)-4-decenoyl (or a mixture containing it) is that, at least partially, the decenoyl compound is transformed into the corresponding decanoyl compound.

As it is appreciated by the skilled technician, the ultimate choice of the specific protecting group depends on the characteristics of the particular amide derivative which is desired. In fact, this amide function of the final compound should be stable at the condition of removal of the protecting group(s).

Since the conditions of removal of the different protecting groups are known, the skilled technician is capable of selecting the proper protecting group.

The formation of "activated esters" is described in general terms in Fieset and Fieser, Reagent for organic synthesis, John Wiley and Sons Inc., pages 129–130 (1967).

Examples of said activated ester forming reagents that can be conveniently used in the process of the invention are those described by R. Schwyzer et al. in Helv. Chim. Acta, 1955, 38, 69–70 and encompass: ClCH₂CN, BrCH₂COOC₂H₅, BrCH(COOC₂H₅)₂, ClCH₂COCH₃,

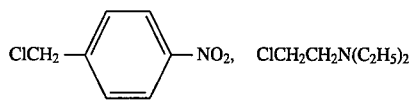

A preferred reagent of this type is chloroacetonitrile. In this case, chloroacetonitrile itself or dimethylformamide (DMF) can be used as preferred solvents.

Generally, inert organic solvents useful for the formation of "activated esters" are those organic aprotic solvents which do not unfavorably interfere with the reaction course and are capable of, at least partially, solubilizing the carboxyacid starting material.

Examples of said inert organic solvents are organic amides, akyl ethers, ethers of glycols and polyols, phosphoramides, sulfoxides and aromatic compounds. Preferred examples of inert organic solvents are: dimethylformamide, dimethoxyethane, hexamethylphosphoramide, dimethylsulfoxide, benzene, toluene and mixtures thereof.

More preferably, the solvent is selected from acetonitrile, dimethylsulfoxide, dimethylformamide. The formation of the activated ester is generally conducted in the presence of a base which does not interfere with the reaction course such as a tri-alkylamine like triethylamine, sodium or potassium carbonate or bicarbonate. Generally, the base is employed in a 2 to 6 molar proportion to the teicoplanin carboxy acid starting material and, preferably, it is used in an about three-fold molar excess. A preferred base is triethylamine.

The "activated ester" forming reagent is used in a large excess over the teicoplanin carboxy acid starting material. It is in general used in a 5 to 35 molar proportion and preferably, it is used in an about 20 to 30 times molar excess. The reaction temperature is between 10° C. and 60° C. and preferably between 15° C. and 30° C. As usual, the reaction time depends on the other specific reaction parameters and may be generally between 3 and 48 hours.

In this case, the reaction course may be followed by HPLC or TLC to determine when the reaction may be considered as completed and the procedures to recover the desired intermediate can be started. The "activated ester" intermediate can be directly used in the same reaction medium where it is prepared, however, in general, it is isolated by precipitation with non-solvents or by extraction with solvents and it is used as such, without further purification, in the next reaction step. If desired, however, it may be purified by column chromatography such as flash column chromatography or reverse-phase column chromatography.

The obtained "activated ester" intermediate is then reacted with a molar excess of the amine derivative of formula II

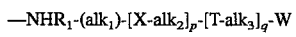    II in the presence of an organic polar solvent at a temperature between 5° C. and 60° C., preferably between 10° C. and 30° C.

The organic polar solvent can be in this case a polar protic solvent or an aprotic one.

Preferred examples of organic polar protic solvents are lower ($C_2$–$C_4$) alkanols such as, ethanol, n-propanol, iso-propanol, n-butanol and the like, or mixtures thereof, preferably used in the dry form.

Preferred examples of organic polar aprotic solvent are N,N-dimethylformamide (DMF), hexamethylphosphoramide (HMPA), or mixtures thereof, 1,3-dimethyl-3,4,5,6-tetrahydro-2(1H) pyrimidone (DMPU), dimethylsulfoxyde (DMSO) or dimethoxyethane (DME).

The reaction of the "activated ester" with the selected amine can be carried out at a temperature between 5° C. and 60° C. but the preferred temperature is generally comprised between 10° C. and 30° C., most preferably between 20° C. and 25° C., while a preferred molar proportion between the "activated ester" intermediate and the amine II as above defined is from 1:5 to 1:30, and more preferably from 1:10 to 1:20. The reaction course may be monitored as usual by TLC or HPLC.

The amide derivative obtained from the amidation reaction is recovered from the reaction solution according to common procedures, for instance, by evaporation of the solvent or by addition of a non-solvent. The removal of the amino-protecting group is usually carried out on the crude product isolated from the amidation reaction.

Examples of procedures for the removal of said protecting groups from teicoplanin derivatives are described for instance in International Application Publication No. WO 88/06600.

If catalytic hydrogenation procedures are used, the reaction is usually carried out in the presence of a diluted aqueous strong acid, preferably a mineral acid, in an organic solvent miscible with said diluted aqueous strong acid. The filtrate from the reaction is then worked for the recovery of either the mineral acid addition salt of the amide of formula I or the corresponding free base. Analogous procedures are followed when the amino-protecting group is a group which can be removed by treating with diluted mineral acids (e.g. Schiff base or a $C_1$–$C_4$ alkoxy carbonyl group) under conditions which do not cause the splitting of the sugar moieties (e.g. low temperatures, short reaction time).

A further procedure for the preparation of a compound of formula I of this invention consists in reacting an $N^{15}$ protected derivative of a $N^{63}$ amide of formula I wherein Y is —NR₁alk₁XH or NR₁-alk₁-[X-alk₂]$_p$-TH with a reactant of the formula r-[alk₂]$_p$-[T-alk₃]$_q$-W or r-[alk₃]$_q$W, respectively, wherein the symbol R₁, alk₁, alk₂, alk₃, X and T are the same as above, r represents halo, methanesulfonyl or tosyl, in the presence of an acid acceptor in an inert solvent. In such cases, p is preferably 1 or 2, q is different from zero and preferably is 1 or 2, X and T preferably represent NH or oxygen, most preferably oxygen. The $N^{15}$ protected derivative of the $N^{63}$ amide referred above are prepared according to the general method for the preparation of the compounds of formula I of this invention.

When a compound of formula I wherein W represents —NR₈R₉— wherein R₈ is defined as above, R₉ is COOR₁₀ and R₁₀ is a ($C_1$–$C_6$)acyloxy-($C_1$–$C_4$)alkyl is desired, it is necessary to react a $N^{15}$ protected derivative of the $N^{63}$ amide wherein W is —NHR₈— being R₈ defined as above with an alpha-acyloxy-alkyl para-nitrophenyl carbonate in the presence of an anhydrous alkaline carbonate such as sodium carbonate.

The alpha-acyloxy-alkyl para-nitrophenyl carbonate can be prepared as described in J. Med. Chem., 31, pages 318–322 (1988).

Some amides of the present invention, such as those of teicoplanin A₂ complex, a single component thereof or any mixture of two or more of said components can be used as the starting material for preparing unitary antibiotic products by means of selective hydrolysis of one or two sugar moieties by following the procedure described in the already cited European Patent No. 119575 and European Patent No. 119574.

An alternative method for the manufacture of compounds of formula I wherein A is hydrogen, B is N-acetyl-beta-D-2-deoxy-2-aminoglucopyranosyl and M is alpha-D-mannopyranosyl consists in hydrolyzing the corresponding amide compounds of formula I wherein A is —N[($C_9$–$C_{12}$) aliphatic acyl[-beta-D- 2-deoxy-2-aminoglucopyranosyl, B is N-acetyl-beta-D-2-deoxy-2-aminoglucopyranosyl and M is alpha-D-mannopyranosyl (i.e. the carboxyamide derivatives of teicoplanin $A_2$ complex or a single component thereof) according to the process described in the European Patent Application Publication No. 146822.

The process consists in contacting the above material with concentrated aqueous organic acid at about room temperature, preferably with aqueous trifluoroacetic acid at a concentration between 75% and 95% at a temperature comprised between 10° C. and 50° C.

An alternative process for preparing the compounds of formula I wherein both A and M are hydrogen and B is N-acetyl-beta-D-2-deoxy-2-aminoglucopyranosyl consists in submitting the compounds of formula I wherein A is N[($C_9$–$C_{12}$) aliphatic acyl]-beta-D- 2-deoxy-2-aminoglucopyranosyl, B is N-acetyl-beta-D-2-deoxy-2-aminoglucopyranosyl and M is alpha-D-mannopyranosyl to an hydrolysis process according to European Patent Application Publication No. 175100.

The process consists in contacting the above starting material with a strong acid in the presence of a polar aprotic organic solvent selected from ethers, ketones and mixture thereof which are liquid at room temperature.

In this latter case as the starting materials can be used also the amide compounds of formula I wherein A is hydrogen, B is N-acetyl-beta-D-2-deoxy-2-aminoglucopyranosyl and M is alpha-D-mannopyranosyl which are obtained according to the hydrolysis process with concentrated aqueous trifluoroacetic acid as described above.

For the isolation of the acid addition salt, the reaction solution resulting from the splitting of the amino-protecting group is generally brought to a pH value between 4 and 7 by addition of an aqueous base, e.g. aqueous sodium hydroxide, and, after evaporation of the solvent under reduced pressure, the resulting solid is separated in the form of an addition salt with the strong acid which has been added during the de-protection step. Such product may be further purified by common techniques e.g. column chromatography, precipitation from solutions by addition of non-solvents, preparative HPLC and similar. The acid addition salt may be converted to the corresponding free base of formula I by suspending or dissolving the acid addition salt in an aqueous solvent which is then brought to an appropriate pH value whereby the free-base form is restored. The product is then recovered, for instance, by extraction with an organic solvent or is transformed into another acid addition salt by adding the selected acid and working up as above.

Sometimes, after the above operation, it may be necessary to submit the recovered product to a common desalting procedure.

For example, column chromatography on controlled pore polydextrane resins (such as SEPHADEX®, chromatography medium LH 20) or silanized silica gel may be conveniently used. After eluding the undesired salts with an aqueous solution, the desired product is eluted by means of linear gradient or step-gradient of a mixture of water and a polar or apolar organic solvent, such as acetonitrile/water from 5% to about 100% acetonitrile and then recovered by evaporation of the solvent or by lyophilization.

A compound of formula I in the free-base form can be transformed into the corresponding acid addition salt by suspending or dissolving the free base form in an aqueous solvent and adding a slight molar excess of the selected acid. The resulting solution or suspension is then lyophilized to recover the desired acid addition salt. Instead of lyophilizing, in some instances, it is possible to recover the final salt through precipitation by addition of a non-solvent mixable with water.

In case the final salt is insoluble in an organic solvent where the free base form is soluble it may be recovered by filtration from the organic solution of the non-salt form after addition of the stoichiometric amount or a slight molar excess of the selected acid.

Representative and suitable acid addition salts of the compounds of formula I include those salts formed by standard reaction with both organic and inorganic acids such as, for example, hydrochloric, hydrobromic, sulfuric, phosphoric, acetic, trifluoroacetic, trichloroacetic, succinic, citric, ascorbic, lactic, maleic, fumaric, palmitic, cholic, pamoic, mucic, campboric, glutaric, glycolic, phthalic, tartaric, lauric, stearic, salicylic, methanesulfonic, benzenesulfonic, sorbic, picric, benzoic, cinnamic and the like acids.

Preferred addition salts of the compounds of this invention are the pharmaceutically acceptable acid addition salts.

With the term "pharmaceutically acceptable acid addition salts" are intended those salts with acids which from biological, manufacturing and formulation standpoint are compatible with the pharmaceutical practice.

Example of acids suitable for the "pharmaceuticaly acid addition salts" includes those listed above.

The compounds of the invention in the form of both the free bases and their acid addition salts are useful as antibacterial agents, both against gram-positive and gram-negative bacteria.

However, the compounds of the invention show a striking good activity against gram-negative bacteria, more particularly against *Pseudomonas aeruginosa*.

In fact, at present, they are the most active derivatives among teicoplanin antibiotics against the microorganisms of this genus. Said activity is particularly relevant for those compounds of the invention having a deglucoteicoplanin core but is remarkable also for the compounds of the invention which have a teicoplanin nucleus.

The antibacterial activity of the compounds of the invention can be demonstrated in vitro by means of standard two-fold dilution tests in microtiter, using DIFCO TODD-HEWITT broth, fermentation broth *Strep. pyogenes* and *Strep. pneumeniae*) or OXOID ISO-SENSITEST broth, fermentation broth (*Staphylococci, Strop. faecalis,* and gram-negative organisms). Broth cultures are diluted enough so that the final inecuium is about $10^4$ colony forming units/ml (CFU/ml). Minimal inhibitory concentration (MIC) is considered as the lowest concentration which shows no visible growth after 18–24 h incubation at 37° C.

The results of the antibacterial testing of representative compounds of the present invention are summarized in Table I.

TABLE I

In vitro activity (MIC microgram/ml)

| Test Organisms | Compounds No. | | | | |
|---|---|---|---|---|---|
| | 6 | 9 | 11 | 21 | 22 |
| *Staphylococcus aureus* TOUR | 0.12 | 0.12 | 0.12 | 0.06 | 0.06 |
| *Staphylococcus epidermidis* ATCC 12228 | 0.06 | 0.06 | 0.06 | 0.06 | 0.03 |
| *Staphylococcus haemolyticus* L 602 | 0.12 | 0.12 | 0.12 | 0.12 | 0.12 |
| *Streptococcus pyogenes* C 203 | 0.06 | 0.06 | 0.06 | 0.12 | 0.12 |
| *Streptococcus pneumoniae* UC 41 | 0.12 | 0.12 | 0.12 | 0.12 | 0.12 |
| *Streptococcus faecalis* ATCC 7080 | 0.12 | 0.12 | 0.12 | 0.12 | 0.12 |
| *Escherichia coli* SKF 12140 | >128 | >128 | 64 | 8 | 1 |
| *Proteus vulgaris* X19H ATCC 881 | >128 | >128 | 128 | 64 | 32 |
| *Pseudomonas aeruginosa* ATCC 10145 | 64 | 64 | 32 | 64 | 8 |

| Test Organisms | Compounds No. | | | | |
|---|---|---|---|---|---|
| | 23 | 24 | 25 | 26 | 27 |
| *Staphylococcus aureus* TOUR | 0.06 | 0.06 | 0.12 | 0.06 | 0.06 |
| *Staphylococcus epidermidis* ATCC 12228 | 0.06 | 0.06 | 0.06 | 0.016 | 0.06 |
| *Staphylococcus haemolyticus* L 602 | 0.06 | 0.06 | 0.12 | 0.06 | 0.12 |
| *Streptococcus pyogenes* C 203 | 0.06 | 0.06 | 0.06 | 0.06 | 0.06 |
| *Streptococcus pneumoniae* UC 41 | 0.12 | 0.12 | 0.12 | 0.12 | 0.12 |
| *Streptococcus faecalis* ATCC 7080 | 0.12 | 0.12 | 0.12 | 0.25 | 0.12 |
| *Escherichia coli* SKF 12140 | 2 | 4 | 2 | 0.5 | 2 |
| *Proteus vulgaris* X19H ATCC 881 | 32 | 128 | 64 | 64 | 64 |
| *Pseudomonas aeruginosa* ATCC 10145 | 8 | 64 | 16 | 2 | 8 |

| Test Organisms | Compounds No. | | | | |
|---|---|---|---|---|---|
| | 29 | 30 | 34 | 39 | 44 |
| *Staphylococcus aureus* TOUR | 0.06 | 0.06 | 0.06 | 0.25 | 0.12 |
| *Staphylococcus epidermidis* ATCC 12228 | 0.016 | 0.06 | 0.06 | 0.06 | 0.06 |
| *Staphylococcus haemolyticus* L 602 | 0.06 | 0.12 | 0.12 | 0.12 | 0.06 |
| *Streptococcus pyogenes* C 203 | 0.06 | 0.06 | 0.06 | 0.12 | 0.06 |
| *Streptococcus pneumoniae* UC 41 | 0.12 | 0.12 | 0.12 | 0.5 | 0.25 |
| *Streptococcus faecalis* ATCC 7080 | 0.12 | 0.12 | 0.12 | 0.5 | 0.25 |
| *Escherichia coli* SKF 12140 | 1 | 4 | 4 | 32 | 4 |
| *Proteus vulgaris* X19H ATCC 881 | 32 | 128 | >128 | >128 | 128 |
| *Pseudomonas aeruginosa* ATCC 10145 | 8 | 16 | 32 | 128 | 16 |

| Test Organisms | Compounds No. | | | |
|---|---|---|---|---|
| | 46 | 47 | 50 | 51 |
| *Staphylococcus aureus* TOUR | 0.5 | 0.12 | 0.12 | 0.12 |
| *Staphylococcus epidermidis* ATCC 12228 | 0.12 | 0.12 | 0.008 | 0.06 |
| *Staphylococcus haemolyticus* L 602 | 8 | 2 | 0.06 | 0.12 |
| *Streptococcus pyogenes* C 203 | 0.06 | 0.06 | 0.06 | 0.06 |
| *Streptococcus pneumoniae* UC 41 | 0.12 | 0.06 | 0.12 | 0.12 |
| *Streptococcus faecalis* ATCC 7080 | 0.25 | 0.12 | 0.12 | 0.25 |
| *Escherichia coli* SKF 12140 | >128 | >128 | 1 | 8 |
| *Proteus vulgaris* X19H ATCC 881 | >128 | >128 | 128 | 128 |
| *Pseudomonas aeruginosa* ATCC 10145 | >128 | >128 | 8 | 32 |

| Test Organisms | Compounds No. | | | |
|---|---|---|---|---|
| | 52 | 53 | 54 | 55 |
| *Staphylococcus aureus* TOUR | 0.12 | 0.06 | 0.5 | 1 |
| *Staphylococcus epidermidis* ATCC 12228 | 0.03 | 0.06 | 0.12 | 0.12 |
| *Staphylococcus haemolyticus* L 602 | 0.12 | 0.06 | 2 | 1 |
| *Streptococcus pyogenes* C 203 | 0.12 | 0.06 | 0.03 | 0.12 |
| *Streptococcus pneumoniae* UC 41 | 0.12 | 0.12 | 0.12 | 0.12 |
| *Streptococcus faecalis* ATCC 7080 | 0.12 | 0.12 | 2 | 1 |
| *Escherichia coli* SKF 12140 | 32 | 8 | >128 | >128 |
| *Proteus vulgaris* X19H ATCC 881 | >128 | 128 | >128 | >128 |
| *Pseudomonas aeruginosa* ATCC 10145 | 128 | 32 | 128 | >128 |

The activity against some multi-resistant clinical isolates of *Pseudomonas aeruginosa* of compounds 22, 23, 25, 26, 27 and 29 is shown in Table II.

TABLE II

| Pseudomonas aeruginosa Strain No. | MIC (microgram/ml) | | | | | |
|---|---|---|---|---|---|---|
| | Compound 22 | Compound 23 | Compound 25 | Compound 26 | Compound 27 | Compound 29 |
| L 1138 | 64 | 64 | 32 | 32 | 64 | 64 |
| L 1348 | 4 | 4 | 4 | 4 | 4 | 8 |
| L 1498 | 64 | 64 | 64 | 64 | 64 | 64 |
| L 1533 | 64 | 128 | 64 | 64 | 64 | 128 |

The activity of the compounds of this invention against *Pseudomonas aeruqinosa* is higher than that of teicoplanin and the closest compounds of European Patent Application Publication No. 218099 and International Patent Application Publication No. WO 88/06600 whose MIC (microgram/ml) against the same microorganism is never lower than 32.

The activity of the compounds of the invention against *Pseudomonas aeruginosa* bacteria is particularly relevant in view of the importance of the infection due to said strain.

Clinical infection with *P. aeruginosa* include local infection, e.g. of wounds (especially burns), the urinary tract, the respiratory tract, the intestine, the eye and the ear, and generalized infections (blood, bone or septicaemic) arising from sites of primary local infection in patients with impaired resistance, and leading to the development of metastatic foci in various organs.

The prognosis for patients who develop Pseudomonas septicemia is poor and some authors report a very high (sometimes 100%) mortality. See for example "Genetics and Biochemistry of Pseudomonas" by P. H. Clarke and M. H. Richmond (Chapter 2), John Wiley and Sons (1975).

Furthermore, the teicoplanin compounds of the invention which are different from deglucoteicoplanin and teicoplanin pseudoaglycons show a remarkable higher in vivo activity for what concerns the oral administration with respect to the teicoplanin amide derivatives known in the art.

The $ED_{50}$ values (mg/kg) of representative compounds of the invention in in vivo tests in mice septicemically infected with *Strep. pyogenes*. C 203, obtained according to the procedure described by V. Arioli et al. (Journal of Antibiotics 29, 511; 1976) are given in table III.

TABLE III

| | In vivo activities | |
|---|---|---|
| | $ED_{50}$ (mg/kg) | |
| Compound No. | s.c. | p.o. |
| 2 | 0.09 | about 60 |
| 6 | 0.05 | 81.2 |
| 9 | 0.06 | about 80 |
| 11 | 0.03 | 81.2 |
| 15 | 0.06 | about 60 |
| 33 | 0.06 | 74.4 |

In vivo Compound 50 was found to be particularly effective in curing mice septicemically infected with *E. coli* after i.v. administration (40 mg/kg, 7/8 surv./treated) and after s.c. administration ($ED_{50}$ ≦38 mg/kg).

In view of the above reported antimicrobial activity, the compounds of the present invention can be employed as the active ingredients of antimicrobial preparations used in human and veterinary medicine for the prevention and treatment of infective diseases caused by pathogenic bacteria which are susceptible to said active ingredients.

In such treatments, these compounds may be employed as such or in the form of mixtures in any proportion.

The compounds of the present invention can be administered orally, topically or parenterally wherein however, the parenteral administration is preferred. Depending on the route of administration, these compounds can be formulated into various dosage forms. Preparations for oral administration may be in the form of capsules, tablets, liquid solutions or suspensions. As known in the art the capsules and tablets may contain in addition to the active ingredient, conventional excipients such as diluents, e.g. lactose, calcium phosphate, sorbitol and the like, lubricants, e.g. magnesium stearate, talc, polyethylene glycol, binding agents, e.g. polyvinylpyrrolidone, gelatin, sorbitol, tragacanth, acacia, flavoring agents, and acceptable disintegrating and wetting agents. The liquid preparations generally in the form of aqueous or oily solutions or suspensions, may contain conventional additives such as suspending agents. For topical use the compounds of the present invention may also be prepared in suitable forms to be applied to the skin, the mucous membranes of the nose and throat or bronchial tissues and may conveniently take the form of creams, ointments, liquid sprays or inhalants, lozenges, or throat paints.

Another advantage of the compounds of the present invention is a marked higher water solubility in a wider range of pH, and, consequently the normal problems for suitable pharmaceutical composition are avoided.

For medication of the eyes or ears, the preparation may be presented in liquid or semi-liquid form formulated in hydrophobic or hydrophilic bases as ointments, creams, lotions, paints, or powders.

For rectal administration the compounds of the invention are administered in the form of suppositories admixed with conventional vehicles, such as, for example, cocoa butter, wax, spermaceti or polyethylenglycols and their derivatives.

Compositions for injection may take such forms as suspensions, solutions, or emulsions in oily or aqueous vehicles, and may contain formulatory agents such as suspending, stabilizing and/or dispersing agents.

Alternatively, the active ingredient may be in powder form for reconstitution at the time of delivery with a suitable vehicle, such as sterile water.

The amount of active principle to be administered depends on various factors such as the size and conditions of the subject to be treated, the route and frequency of administration, and the causative agent involved.

The compounds of the invention are generally effective at a dosage comprised between about 0.5 and about 30 mg of active ingredient per kg of body weight, preferably divided in 2 to 4 administrations per day. Particularly desirable compositions are those prepared in the form of dosage units containing from about 20 to about 300 mg per unit.

The following examples illustrate the manner in which the invention can be practiced but, as such, should not be construed as limiting its overall scope.

EXAMPLES—EXPERIMENTAL SECTION

Legenda

In the following examples the starting material may be teicoplanin $A_2$ complex (TGA), a single component thereof or any mixture of two or more of said components.

The typical complex mixture essentially consists of five components corresponding to formula I above wherein the aliphatic acyl moieties of the beta-D-2-deoxy-2-aminoglucopyranosyl radical represented by the symbol A are respectively:

Z-(4)-decenoyl ($AC_1$), 8-methylnonanoyl ($AC_2$), decanoyl ($AC_3$), 8-methyldecanoyl ($AC_4$) and 9-methyldecanoyl ($AC_5$), B is N-acetyl-beta-D-2-deoxy-2-aminoglucopyranosyl (AcGlu)

M is alpha-D-mannopyranosyl (Man) and

Y is OH.

This mixture is identified by the acronym $TGAC_{1-5}$. When one of the single components of said mixture is employed as the starting material it is identified as follows: $TGAC_1$, $TGAC_2$, $TGAC_3$, $TGAC_4$ or $TGAC_5$, depending on the specific aliphatic acyl rest of the above mentioned aminoglucopyranosyl radical.

When a mixture of one or more components is used it is indicated according to the same system as for the complex. For instance, the acronym $TGAC_{2-5}$ indicates the mixture of the components 2 to 5 wherein component 1 is no longer present. This mixture is currently obtained when the catalytic hydrogenation saturates the double bond of component 1 transforming it into component 3. The acronym $TGAC_{2,3}$ indicates a mixture of the components 2, 3 and the acronym $TGAC_{4,5}$ indicates a mixture of the components 4 and 5.

The antibiotic L 17392 (i.e. the aglycon of teicoplanin) is represented by the acronym DTG, while the pseugoaglycons L 17054 and L 17046 are represented respectively by the terms TGA3-1 and TGA3-2 and the de-mannosyl pseudoaglycone (European Patent Application Publication No. 301247) by the term DM-TGAC.

The resulting end products in the following tables are identified by reference to formula I above with the indication for the symbol A of the particular aliphatic acyl substituent of the beta-D-2-deoxy-2-aminoglucopyranosyl radical (A/AC) by using the conventional terms $AC_1$, $AC_2$, $AC_3$, $AC_4$, $AC_5$ as explained above. When a mixture of two or more components is obtained, this is shown through the same formal system as above.

EXAMPLES 1–30

When the $N^{63}$-carboxyamides of the mixtures $TGAC_{2-5}$ are desired the following procedures are used:

A—Preparation of $N^{15}$-benzyloxycarbonyl (CBZ) teicoplanin $A_2$ complex and single components 1 to 5 thereof A solution of 4.5 ml of benzyl chloroformate in 10 ml of dry acetone is added dropwise at room temperature to a stirred solution of 45 g (about 24 mmol) of teicoplanin $A_2$ complex (or a single component 1 to 5 thereof) and of 6 ml (about 44 mmol) of triethylamine (TEA) in 300 ml of dimethylformamide (DMF). After about 60 min, 600 ml of ethyl ether is added and the precipitate (about 59 g) is collected by filtration and re-dissolved in 2.5 L of a mixture acetone: water, 1:1 (v/v). The resulting solution is concentrated at 35° C. under reduced pressure to a volume of about 1.6 L, then it is extracted with 1.6 L of ethyl ether which is separated and discarded.

The aqueous layer is adjusted to pH 4.8 with glacial acetic acid and extracted with 1.5 L of n-butanol. The organic layer is separated, washed with 1.5 L of water (2×750 ml), then it is concentrated to a volume of about 200 ml at 45° C. under reduced pressure. On adding ethyl acetate (about 800 ml) a solid separates which is collected by filtration, washed with ethyl ether (about 500 ml) and dried at room temperature in vacuo overnight, yielding 45.7 g (about 96%) of pure title compound.

B—Preparation of $N^{15}$-CBZ-teicoplanin $A_2$ complex and single components 1 to 5 thereof, cyanomethyl ester To a stirred solution of 45 g (about 22 mmol) of $N^{15}$-CBZ-teicoplanin $A_2$ complex (or a single component thereof) in 450 ml of DMF, 5.25 l (about 37 mmol) of TEA and 60 ml of chloroacetonitrile are added at room temperature. After 20 h, the reaction mixture is poured into 4.5 L of ethyl acetate and the precipitate (about 50 g) is collected by filtration and re-dissolved in 900 ml of a mixture methanol: water 1:1 (v/v). The resulting solution is adjusted to pH 5.5 with glacial acetic acid, then 1.1 L of n-butanol is added. Most of the methanol is evaporated at 35° C. under reduced pressure to obtain a mixture (about 1.5 L) of n-butanol and water from which the organic layer is separated, washed with 500 ml of water and concentrated at 40° C. under reduced pressure to a volume of about 200 ml. On adding 800 ml of ethyl acetate a solid separates which is collected, washed with 500 ml of ethyl ether and dried at 35° C. in vacuo overnight to give 44.2 g (about 98% yield) of pure title compound.

C—Preparation of $N^{63}$-carboxyamides of $N^{15}$-CBZ-teicoplanin $A_2$ complex and single components 1 to 5 thereof A solution of 16 g (about 8 mmol) of $N^{15}$-CBZ-teicoplanin $A_2$ complex (or a single component 1 to 5 thereof), cyanomethyl ester and of a large excess (from 50 to 100 mmol) of the proper amine reactant in 160 ml of DMF or DMSO is stirred at room temperature for 60–120 min, afterwards 160 ml of absolute ethanol is added followed by 1.5 L of ethyl acetate. A solid separates which is collected by filtration and washed with 500 ml of ethyl ether, then it is dried at room temperature in the air to obtain a powder (yields generally >85%) which is enough pure (HPLC titre generally >90%) for the next hydrogenation step.

D—Preparation of $N^{63}$-carboxyamides of teicoplanin $A_2$ complex and single components 2 to 5 thereof The product obtained as described above (5 mmol) is dissolved in 500 ml of a mixture methanol: 0.04N hydrochloric acid 7/3 (v/v) and the resulting solution is hydrogenated at room temperature and pressure in the presence of 5% Pd/C (5 g). As soon as the reaction is completed (HPLC) the catalyst is removed by filtration through a panel of celite (BDH 545). The clear filtrate is adjusted to pH 6.5 with 1N NaOH and 500 ml of n-butanol is added. The resulting mixture is concentrated, at 40° C. under reduced pressure, to a volume of about 150 ml, then 350 ml of ethyl ether is added and the precipitate is collected by filtration. When the reaction is carried out in a substrate containing a derivative corresponding to the component 1 of teicoplanin $A_2$ complex, the relative end product does not contain the component 1 carboxyamide since it is almost completely transformed into component 3 carboxyamide.

E—Purification of the products by reverse phase column chromatography

Crude products obtained as described above (10 g) are dissolved in a mixture (300 ml) acetonitrile: water 1:1 (v/v). Water is then added until a cloudy solution forms (in any case no more than 700 ml of water is added) which is loaded at the top of a column of 500 g of silanized Silica-gel (0.06–0.2 min; Merck Co.) prepared in the same solvent mixture (i.e., $CH_3CN$ and $H_2O$ in the ratio calculated on the base of the amount of $H_2O$ added to obtain the above cloudy solution) as obtained at the beginning of the precipitation. The column is developed with a linear gradient, from 10% to 80% of acetonitrile in water previously adjusted to pH 3.2 with glacial acetic acid, in 15 h at the rate of 400 ml/h while collecting 25 ml fractions which are monitored by HLPC. Those fractions containing the desired pure product are combined and enough n-butanol is added to obtain, after concentration at 45° C. under vacuum a cloudy dry butanolic solution. On adding three volumes, of ethyl ether a solid separates which is collected, washed with ethyl ether and dried at room temperature in vacuo overnight to give pure final compound.

The compounds of the invention (Table IV) are thus obtained as the free bases (FB) when the only basic function present in the molecule is the free amino group in the position 15 of teicoplanin $A_2$ complex, or when the additional amino group introduced with the amide substituent is not enough basic to form an acid addition salt with acetic acid. Otherwise they are recovered as the acetates.

Preparation of the corresponding hydrochlorides is carried out, when this acid addition salt form is required, according to the following procedures:

1 mmol of an amide of teicoplanin $A_2$ complex (or a single component thereof), either as the free base or as the acetate, is dissolved in 10 ml of DMF. A 10% molar excess of 10N HCl (0.11 ml for one amino function to be salified, 0.22 ml for two amino groups, etc.,) is then added under stirring at 5° C., afterwards 40 ml of ethyl ether is added. The precipitate which forms is then collected by filtration, washed with ethyl ether and dried at room temperature in vacuo overnight (yields >95%).

When the $N^{63}$-carboxyamides of component 1 ($TGAC_1$) of teicoplanin $A_2$ complex (or the mixture $TGAC_{1-5}$) are desired, the following procedures are used:

A'—Preparation of $N^{15}$-tert-butyloxycarbonyl (t-BOC) teicoplanin $A_2$ complex and single components 1 to 5 thereof A solution of 10 g (about 5 mmol) of teicoplanin $A_2$ complex or a single component 1 to 5 thereof, 1.2 ml (about 8.5 mmol) of triethylamine (TEA) and 2.4 g (about 8 mmol) of tert-butyl-2,4,5-trichlorophenylcarbonate in 100 ml of dimethylformamide (DMF) is stirred at room temperature for 24 h. Then it is poured into 200 ml of water. The resulting cloudy solution is adjusted at pH 3 with 1N HCl and it is extracted with 600 ml of a mixture n-butanol/ethyl acetate 35:65 (v/v). The organic layer is separated, washed with water (2×100 ml), then it is concentrated to a volume of about 100 ml at 45° C. under reduced pressure. On adding ethyl acetate (about 400 ml) a solid separates which is collected by filtration, washed with ethyl ether (about 200 ml) and dried at room temperature in vacuo overnight, yielding 10.3 g (about 98%) of pure title compound.

B'—Preparation of $N^{15}$-t-BOC-teicoplanin $A_2$ complex and a single component 1 to 5 thereof, cyanomethyl ester Substantially following the above procedure B, the title compound was obtained (about 98% yield) from t-BOC-teicoplanin $A_2$ complex.

C'—Preparation of $N^{63}$-carboxyamides of $N^{15}$-t-BOC-teicoplanin $A_2$ complex and a single component 1 to 5 thereof Substantially following the above procedure C, but using dimethylsulfoxide (DMSO) instead of DMF as the preferred solvent, the title compounds were obtained from $N^{15}$-BOC-teicoplanin $A_2$ complex, cyanomethyl ester, substantially with the same yields (generally >85%) and purity (HPLC titre generally >90%).

D'—Preparation of $N^{63}$-carboxyamides of teicoplanin $A_2$ complex or a single component thereof The product ($N^{63}$-carboxyamide of $N^{15}$-t-BOC-teicoplanin $A_2$ complex or a single component thereof) (4 mmol) is dissolved in 40 ml of dry trifluoroacetic acid (TFA) at 10° C. As soon as a clear solution is formed (about 2 min) (in any case no more than 5 min after the addition of TFA), the reaction mixture is diluted with 40 ml of methanol while cooling at 10° C. On adding 420 ml of ethyl ether a precipitate separates which is collected by filtration and washed with ethyl ether (5×200 ml).

Purification of the products is readily carried out by dissolving the crude product (5 g) in a mixture (150 ml) acetonitrile/water 1:1 (v/v) , adjusting the resulting solution at pH 6 with 1N NaOH and after diluting with water by following the same chromatographic procedure as described above (E) .

When the $N^{63}$-carboxyamides of deglucoteicoplanin (DTG) are desired the following procedures are used:

A"—Preparation of $N^{15}$-tert-butyloxycarbonyl (t-Boc) deglucoteicoplanin

To a stirred solution of 45 g (about 37 mmol) of antibiotic L 17392 (deglucoteicoplanin) in 600 ml of DMF, 19.3 g (about 65 mmol) of tert-butyl-2,4,5-trichlorophenylcarbonate and 10.2 ml (about 74 mmol) of TEA are added. The reaction mixture is stirred at room temperature for 24 h afterwards it is pured into 1.5 L of water. The resulting solution is adjusted to pH 3 with 1 N hydrochloric acid, then it is extracted with 3 L of a mixture ethyl acetate: n-butanol 2:1 (v/v). The organic layer is separated, washed with 1 L of water, then it is concentrated at 40° C. under vacuum to a volume of about 300 ml. On adding 700 ml of ethyl ether, a solid separates which is collected by filtration, washed with 200 ml of ethyl ether and dried at room temperature in vacuo overnight, yielding 44 g (92%) of pure title compound.

B"—Preparation of $N^{15}$-t-BOC-deglucoteicoplanin cyanomethyl ester

A solution of 44 g (about 33 mmol) of $N^{15}$-t-BOC deglucoteicoplanin, 4.7 ml (about 34 mmol) of TEA and 44 ml of chloroacetonitrile in 440 ml of DMF is stirred at room temperature for 20 h, afterwards 1 L of ethyl acetate is added and the precipitate is collected by filtration. It is re-dissolved (about 46 g) in 1.5 L of a mixture methanol: water 1:2 (v/v) and the resulting solution is adjusted to pH 5.6 with glacial acetic acid.

After adding 2 L of n-butanol, the most methanol is evaporated at 30° C. under vacuum and the organic layer is separated, washed with 1 L of water, then it is concentrated at 35° C. under vacuum to a final volume of about 300 ml. On adding 700 ml of ethyl ether, a solid separates which is collected by filtration, washed with 500 ml of ethyl ether, then it is dried at room temperature in vacuo overnight to give 42.5 g (96%) of pure title compound.

C"—Preparation of $N^{63}$-carboxyamides of $N^{15}$-t-BOC deglucoteicoplanin

To a stirred solution of 14 g (about 10 mmol) of $N^{15}$-t-BOC-deglucoteicoplanin and of a large excess (from 100 to 150 mmol) of the proper reactant amine in 200 ml of DMF, 8.9 ml (about 150 mmol) of glacial acetic acid is added at room temperature. (The molar amount of glacial acetic acid depends on the structure of the reactant amine. In fact, for one mmol of amine, 0.5 mmol of glacial acetic acid is required when the amine does not contain additional basic functions, 1 mmol of glacial acetic acid when the amine contain one additional basic function, 2 mmol when the amine contain two additional basic functions, etc. Although the presence of acetic acid is unnecessary for the condensation, it is sometimes suitable to avoid side epimerization of the molecule at the $C_3$ position which might occur under basic conditions.

Furthermore, the presence of the acid does not influence the rate of the condensation reaction in the majority of cases.

After 3–6 h (the reaction, except a few cases, is in general completed within 3 h), 600 ml of ethyl acetate is added and the precipitate is collected by filtration, washed with 200 ml of ethyl ether and dried at room temperature in vacuo overnight to give a product which is enough pure for the next deprotection step (yields >75%).

D"—Preparation of $N^{63}$-carboxyamides of deglucoteicoplanin

A solution of 1 mmol of product obtained as described above, which has in general a HPLC titre >85% and contain some acetate of the reactant amine as the main impurity, in 25–30 ml of anhydrous trifluoroacetic acid (TFA) is stirred at room temperature for 20 min, then solvent is evaporated at 25° C. under reduced pressure. The oily residue is re-dissolved in 50 ml of a mixture water: acetonitrile 6:4 (v/v) and the resulting solution is diluted with water until precipitation starts. The suspension thus obtained is adjusted to pH 3.0 with 1N hydrochloric acid (if necessary) and the resulting solution is loaded at the top of a column of 100 g of silanized Silica-gel (0.06–0.2 min; Merck Co.) in water.

E"—Purification of the products by reverse phase column chromatography

The column loaded with the product, as described above, is developed with 1 L Of water, then elution is performed with a linear gradient from 10% of acetonitrile in water to 50% of acetonitrile in 0.01N hydrochloric acid, in 15 h at the rate of 200 ml/h, while collecting 10 ml fractions. Those fractions containing pure product are poled and enough n-butanol is added to obtain, after concentration of the resulting mixture, a cloudy dry butanolic solution (30–100 ml). On adding three volumes of ethyl ether, a solid separates which is collected by filtration, washed with ethyl ether and dried at room temperature in vacuo for 2–3 days to yield pure final amides of deglucoteicoplanin as the hydrochlorides.

The corresponding trifluoroacetates are obtained by following the above chromatographic procedure of purification but eluting with a linear gradient from 10% to 60% of acetonitrile in water and maintaining pH of the eluent at 2.5 adding trifluoroacetic acid.

By using the appropriate reagents TGAC, a single component thereof, DTG or DMTGAC and an amine of formula $$-NHR_1\text{-alk}_1\text{-}[X\text{-alk}_2]_p\text{-}[T\text{-alk}_3]_q\text{-w} \qquad II$$

under the conditions described above the compounds represented in Table IV, are obtained.

TABLE IV

TGA, DMTGAC and DTG carboxyamide derivatives

| Comp. No. | Teicoplanin staring material | Reagents Amine | A/AC | B | M | Y | End product of formula I (R = H) |
|---|---|---|---|---|---|---|---|
| 1 | TGAC$_{2-5}$ | NH$_2$(CH$_2$)$_2$—NH(CH$_2$)$_2$—NH$_2$ | AC$_2$ | AcGlu | Man | —NH(CH$_2$)$_2$—NH(CH$_2$)$_2$—NH$_2$ |
| 2 | TGAC$_{2-5}$ | NH$_2$(CH$_2$)$_2$—NH(CH$_2$)$_3$—NH$_2$ | AC$_{2-5}$ | AcGlu | Man | —NH(CH$_2$)$_2$—NH(CH$_2$)$_3$—NH$_2$ |
| 3 | TGAC$_{2-5}$ | NH$_2$(CH$_2$)$_3$—NH(CH$_2$)$_3$—NH$_2$ | AC$_{2-5}$ | AcGlu | Man | —NH(CH$_2$)$_3$—NH(CH$_2$)$_3$—NH$_2$ |
| 4 | TGAC$_2$ | NH$_2$(CH$_2$)$_2$—NH(CH$_2$)$_3$—NH$_2$ | AC$_{2-5}$ | AcGlu | Man | —NH(CH$_2$)$_2$—NH(CH$_2$)$_3$—NH$_2$ |
| 5 | TGAC$_2$ | NH$_2$(CH$_2$)$_3$—NH(CH$_2$)$_4$—NH$_2$ | AC$_{2-5}$ | AcGlu | Man | —NH(CH$_2$)$_3$—NH(CH$_2$)$_4$NH$_2$* |
| 6 | TGAC$_2$ | NH$_2$(CH$_2$)$_3$—NH(CH$_2$)$_4$—NH$_2$ | AC$_2$ | AcGlu | Man | —NH(CH$_2$)$_3$—NH(CH$_2$)$_4$NH$_2$* |
| 7 | TGAC$_2$ | NH$_2$(CH$_2$)$_2$—H(CH$_2$)$_3$NH(CH$_2$)$_2$NH$_2$ | AC$_2$ | AcGlu | Man | —NH(CH$_2$)$_2$—NH(CH$_2$)$_3$NH(CH$_2$)$_2$NH |
| | *in admixture with —NH(CH$_2$)$_4$NH(CH$_2$)$_3$—NH$_2$ | | | | | |
| 8 | TGAC$_2$ | NH$_2$(CH$_2$)$_3$—NH(CH$_2$)$_2$—NH(CH$_2$)$_3$NH$_2$ | AC$_2$ | AcGlu | Man | —NH(CH$_2$)$_3$—NH(CH$_2$)$_2$—NH(CH$_2$)$_3$NH$_2$ |
| 9 | TGAC$_2$ | NH$_2$(CH$_2$)$_3$—NH(CH$_2$)$_3$NH(CH$_2$)$_3$—NH$_2$ | AC$_2$ | AcGlu | Man | —NH(CH$_2$)$_3$—NH(CH$_2$)$_3$NH(CH$_2$)$_3$—NH$_2$ |
| 10 | TGAC$_{2-5}$ | NH$_2$(CH$_2$)$_3$—NH(CH$_2$)$_4$NH(CH$_2$)$_3$—NH$_2$ | AC$_2$ | AcGlu | Man | —NH(CH$_2$)$_3$—NH(CH$_2$)$_4$NH(CH$_2$)$_3$—NH$_2$ |
| 11 | TGAC$_{1-5}$ | NH$_2$(CH$_2$)$_3$—NH(CH$_2$)$_4$NH(CH$_2$)$_3$—NH$_2$ | AC$_{2-5}$ | AcGlu | Man | —NH(CH$_2$)$_3$—NH(CH$_2$)$_4$NH(CH$_2$)$_3$—NH$_2$ |
| 12 | TGAC$_2$ | NH$_2$(CH$_2$)$_2$NH(CH$_2$)$_2$NH(CH$_2$)$_2$—NH$_2$ | AC$_{2-5}$ | AcGlu | Man | —NH(CH$_2$)$_2$—NH(CH$_2$)$_2$NH(CH$_2$)$_2$—NH$_2$ |
| 13 | TGAC$_{2-5}$ | NH$_2$(CH$_2$)$_3$—NH(CH$_2$)$_2$NH(CH$_2$)$_3$—NH$_2$ | AC$_{2-5}$ | AcGlu | Man | —NH(CH$_2$)$_2$—NH(CH$_2$)$_2$NH(CH$_2$)$_2$—NH$_2$ |
| 14 | TGAC$_2$ | NH$_2$(CH$_2$)$_2$—N[(CH$_2$)$_2$NH$_2$]$_2$ | AC$_2$ | AcGlu | Man | —NH(CH$_2$)$_2$—N[(CH$_2$)$_2$NH$_2$]$_2$ |
| 15 | TGAC$_2$ | NH$_2$(CH$_2$)$_3$—N⟨  ⟩N—(CH$_2$)$_3$—NH$_2$ | AC$_2$ | AcGlu | Man | —NH(CH$_2$)$_3$—N⟨  ⟩N—(CH$_2$)$_3$—NH$_2$ |
| 16 | TGAC$_2$ | NH$_2$(CH$_2$)$_2$[NH(CH$_2$)$_2$]$_3$NH(CH$_2$)$_2$NH$_2$ | AC$_2$ | AcGlu | Man | —NH(CH$_2$)$_2$[NH(CH$_2$)$_2$]NH(CH$_2$)$_2$NH$_2$ |
| 17 | TGAC$_2$ | NH—CH(CH$_3$)CH$_2$—[O—CH$_2$CH(CH$_3$)]$_5$O—CH$_2$CH(CH$_3$)—NH$_2$ | AC$_2$ | AcGlu | Man | NH—CH(CH$_3$)CH$_2$—[O—CH$_2$CH(CH$_3$)]$_5$O—CH$_2$CH(CH$_3$)—NH$_2$* |
| 18 | TGAC$_2$ | NH$_2$—CH(CH$_3$)CH$_2$—[O—(CH$_2$)$_2$]$_{11}$O—CH$_2$CH(CH$_3$)—NH$_2$ | AC$_2$ | AcGlu | Man | —NHCH(CH$_3$)CH$_2$—[O—(CH$_2$)$_2$]$_{11}$O—CH$_2$CH(CH$_3$)—NH$_2$ |
| 19 | TGAC$_2$ | HN⟨  ⟩N—(CH$_2$)$_3$—N(CH$_3$)$_2$ | AC$_2$ | AcGlu | Man | —N⟨  ⟩N—(CH$_2$)$_3$—N(CH$_3$)$_2$ |
| 20 | DM-TGAC$_2$ | NH$_2$(CH$_2$)$_3$—NH(CH$_2$)$_4$—NH(CH$_2$)$_3$—NH$_2$ | AC$_2$ | AcGlu | H | —NH(CH$_2$)$_3$—NH(CH$_2$)$_4$—NH(CH$_2$)$_3$—NH$_2$ |
| | *in admixture with —NHCH(CH$_3$)CH$_2$|OCH[(CH$_3$)CH$_2$]$_5$OCH$_2$(CH$_3$)NH$_2$ | | | | | |
| 21 | DTG | NH$_2$(CH$_2$)$_2$NH(CH$_2$)$_2$—NH$_2$ | H | H | H | —NH(CH$_2$)$_2$NH(CH$_2$)$_2$—NH$_2$ |
| 22 | DTG | NH$_2$(CH$_2$)$_2$NH(CH$_2$)$_3$—NH$_2$ | H | H | H | —NH(CH$_2$)$_2$NH(CH$_2$)$_3$—NH$_2$ |
| 23 | DTG | NH$_2$(CH$_2$)$_3$NH(CH$_2$)$_4$NH$_2$ | H | H | H | —NH(CH$_2$)$_3$NH(CH$_2$)$_4$—NH$_2$* |
| 24 | DTG | NH$_2$(CH$_2$)$_2$NH(CH$_2$)$_2$NH(CH$_2$)$_3$NH$_2$ | H | H | H | —NH(CH$_2$)$_3$NH(CH$_2$)$_2$NH(CH$_2$)$_3$—NH$_2$ |
| 25 | DTG | NH$_2$(CH$_2$)$_3$NH(CH$_2$)$_3$NH(CH$_2$)$_3$—NH$_2$ | H | H | H | —NH(CH$_2$)$_3$NH(CH$_2$)$_3$NH(CH$_2$)$_3$—NH$_2$ |
| 26 | DTG | NH$_2$(CH$_2$)$_3$NH(CH$_2$)$_4$NH(CH$_2$)$_3$—NH$_2$ | H | H | H | —NH(CH$_2$)$_3$NH(CH$_2$)$_4$NH(CH$_2$)$_3$—NH$_2$ |
| 27 | DTG | NH$_2$(CH$_2$)$_3$NH(CH$_2$)$_3$—NH$_2$ | H | H | H | —NH(CH$_2$)$_3$NH(CH$_2$)$_3$—NH$_2$ |
| | *in admixture with —NH(CH$_2$)$_4$NH(CH$_2$)$_3$—NH$_2$ | | | | | |
| 28 | DTG | NH$_2$(CH$_2$)$_2$NH(CH$_2$)$_2$NH(CH$_2$)$_2$—NH$_2$ | H | H | H | —NH(CH$_2$)$_2$NH(CH$_2$)$_2$NH(CH$_2$)$_2$—NH$_2$ |

TABLE IV-continued

TGA, DMTGAC and DTG carboxyamide derivatives

| Comp. No. | Teicoplanin staring material | Reagents Amine | A/AC | B | M | Y | End product of formula I (R = H) |
|---|---|---|---|---|---|---|---|
| 29 | DTG | $NH_2(CH_2)_2N[(CH_2)_2NH_2]_2$ | H | H | H | $-NH(CH_2)_2N[(CH_2)_2NH_2]_2$ | |
| 30 | DTG | $NH_2(CH_2)_3-N\bigcirc N-(CH_2)_3-NH_2$ | H | H | H | $-NH(CH_2)_3-N\bigcirc N-(CH_2)_3-NH_2$ | |

EXAMPLE 31

Preparation of the compound 31 of formula I (R = H, A/AC = AC$_{2-5}$, B = AcGlu, M = Man,

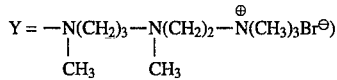

A solution of 2 g (about 1 mmol) of N$^{15}$-CBZ-teicoplanin A$_2$ complex, cyanomethyl ester, prepared as described above and 2 ml of 1,3-dimethyl-1,3-propanediamine in 20 ml of DMF is stirred at room temperature for 2 h, afterwards 20 ml of absolute ethanol is added followed by 200 ml of ethyl acetate. A solid separates which is collected by filtration, washed with 50 ml of ethyl ether and dried in vacuo at room temperature overnight, to yield 1.95 g of pure N$^{15}$-CBZ-teicoplanin A$_2$ complex, 1-methyl-3-(methylamino)propyl-amide.

To a stirred solution of 1.37 g (0.65 mmol) of the above compound in 100 ml of dry methanol, 1 g (9.4 mmol) of anhydrous sodium bicarbonate and 2.5 g (10.1 mmol) of 2-bromoethyl trimethylammonium bromide are added at room temperature. The reaction mixture is stirred at 45° C. for three days, then it is cooled to 10° C. and poured into 100 ml of water. Methanol is evaporated at 30° C. under reduced pressure and the aqueous phase is extracted with 300 ml of a mixture n-BuOH/EtOAc 1/2 (v/v). The organic layer is separated and concentrated at 40° C. under reduced pressure to a small volume (about 20 ml). On adding 180 ml of ethyl ether, the precipitated solid (1.12 g of N$^{15}$-CBZ precursor of the title compound) is collected and hydrogenareal under the same conditions described in Example 1, to give 0.45 g of compound 31.

EXAMPLE 32

Preparation of the compound 32 of formula I (R = H, A/AC = H, B = H, M = H,

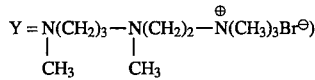

Following the same procedure described in Example 31 above but using a solution of 2 g of N$^{15}$-CBZ-deglucoteicoplanin, cyanomethyl ester, the compound 32 is obtained.

EXAMPLE 33

Preparation of the compound 33 of formula I (R=H, A/AC=AC$_{2-5}$, B=AcGlu, M=Man, Y=-NH(CH$_2$)$_3$NH(CH$_2$)$_4$NHCOOCH(CH$_3$)OCOCH$_3$ in admixture with Y=-NH(CH$_2$)$_4$NH(CH$_2$)$_3$NHCOOCH(CH$_3$)OCOCH$_3$)

To a stirred solution of 2 g (0.9 mmol) of N$^{15}$-CBZ derivative of compound 5 (prepared as described in Example 1 above), in 50 ml of dry DMF, 1.2 g (11 mmol) of anhydrous sodium carbonate and 2.7 g (10 mmol) of alpha-acetoxy-ethyl para-nitrophenyl carbonate are added at room temperature. After 3 h, the reaction mixture is poured into 500 ml of ethyl acetate and the precipitated solid is collected, washed with 100 ml of ethyl acetate and hydrogenated as described in Example 1 above, to yield 0.57 g of the title compound 33.

EXAMPLE 34

Preparation of the compound 34 of formula I (R=H, A/AC=H, B=H, M=H, Y=NH(CH$_2$)$_3$NH(CH$_2$)$_4$NHCOOCH(CH$_3$)OCOCH$_3$ in admixture with Y=NH(CH$_2$)$_4$NH(CH$_2$)$_3$NHCOOCH(CH$_3$)OCOCH$_3$)

Following the procedure as described in Example 32 but using 2 g of N$^{15}$-CBZ derivative of compound 23, 0.6 g of compound 34 are prepared.

EXAMPLES 35–36

Preparation of compound 35 of formula I (R = H, A/AC = AC$_{2-5}$, B = AcGlu, M = Man,

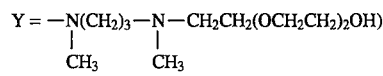

and of compound 36 of formula I (R = H, A/AC = AC$_{2-5}$, B = AcGlu, M = Man,

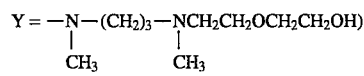

To a stirred suspension of 5.3 g (about 2.5 mmol) of N$^{15}$-CBZ-teicoplanin A$_2$ in 560 ml of methanol, 1-methyl-3-(methylamino) propyl-amide (prepared as described above in Example 31), 17 ml of the proper chloroethoxy-hydroxyethyl reagent of formula ClCH$_2$CH$_2$(OCH$_2$CH$_2$)$_2$OH and ClCH$_2$CH$_2$OCH$_2$CH$_2$OH respectively and 1.86 g (13.5 mmol) of potassium carbonate are added at room temperature. After stirring at 45° C. for 3 h, the reaction mixture is cooled to 15° C. and adjusted at pH 6 with 1N HCl. Methanol is evaporated at 30° C. under reduced pressure, and the solid residue is hydrogenated as described in Example 1 to yield 1.9 g of compound 35 or 0.97 g of compound 36.

EXAMPLES 37–41

Preparation of TGA3-1 amide derivatives

A solution of 4 g (about 2 mmol) of the proper amide derivative of a teicoplanin A$_2$ complex or a single component thereof prepared as described above and reported in table V below, in 100 ml of 90% aqueous trifluoroacetic acid is stirred at room temperature for 2h; afterwards the solvents are evaporated and the oily residue is re-dissolved in 200 ml of H$_2$O. After adjusting at pH 8, the resulting solution is loaded on a column of 400 g of silanized silicagel in H$_2$O. Chromatography is performed as described above in Example 1 to give the title compounds.

TABLE V

TGA3-1 carboxyamide derivatives

| Comp. No. | Reagent Compound No. | A/AC | B | M | Y |
|---|---|---|---|---|---|
| 37 | 1 | H | AcGlu | Man | —NH(CH$_2$)$_2$NH(CH$_2$)$_2$NH$_2$ |
| 38 | 5 | H | AcGlu | Man | —NH(CH$_2$)$_3$—NH(CH$_2$)$_4$—NH$_2$* |
| 39 | 10 | H | AcGlu | Man | —NH(CH$_2$)$_3$NH(CH$_2$)$_4$NH(CH$_2$)$_3$—NH$_2$ |
| 40 | 12 | H | AcGlu | Man | —NH(CH$_2$)$_2$NH(CH$_2$)$_2$NH(CH$_2$)$_2$—NH$_2$ |
| 41 | 14 | H | AcGlu | Man | —NH(CH$_2$)$_2$N[(CH$_2$)$_2$NH$_2$]$_2$ |

(*)in admixture with —NH(CH$_2$)$_4$—NH(CH$_2$)$_3$—NH$_2$

EXAMPLES 42–45

Preparation of TGA3-2 amide derivatives

A suspension of 4 g (about 2 mmol) of the proper amide derivative of a teicoplanin compound prepared as described above and reported in table VI below, in 80 ml of 1,2-dimethoxyethane (DME) is stirred at room temperature for 2 days, while bubbling dry HCl, afterwards the insoluble matter is collected by filtration. Purification by column chromatography as described above (Example 1) yields the title compounds.

TABLE VI

TGA3-2 carboxyamide derivatives

| Comp. No. | Reagent Compound No. | A/AC | B | M | Y |
|---|---|---|---|---|---|
| 42 | 1 | H | AcGlu | H | —NH(CH$_2$)$_2$—NH(CH$_2$)$_2$NH$_2$ |
| 43 | 5 | H | AcGlu | H | —NH(CH$_2$)$_3$—NH(CH$_2$)$_4$—NH$_2$* |
| 44 | 10 | H | AcGlu | H | —NH(CH$_2$)$_3$NH(CH$_2$)$_4$—NH(CH$_2$)$_3$—NH$_2$ |
| 45 | 12 | H | AcGlu | H | —NH(CH$_2$)$_2$—NH(CH$_2$)$_2$—NH(CH$_2$)$_2$—NH$_2$ |

(*)in admixture with —NH(CH$_2$)$_4$—NH(CH$_2$)$_3$—NH$_2$

EXAMPLES 46–55

A'''—General Procedure (by employing diphenyl phosphorazide)

To a stirred solution of 6 mmol of teicoplanin A2, or a single component thereof (or a mixture of its components in any proportion), or N$^{15}$-tert-butyloxycarbonyl (t-BOC) deglucoteicoplanin in 60 mL of dimethylsulfoxide (DMSO), 30 mmol of the appropriate intermediate amine (prepared as described below) and 10 mmol of diphenyl phosphorazidate (DPPA) are added at 0°–5° C. After stirring at room temperature overnight, 240 mL of ethyl acetate is added and the precipitated solid is collected and purified by reverse phase column chromatography as described previously (Method E), thus obtaining pure TGAC amides or N$^{15}$-t-BOC-deglucoteicoplanin amides (BOC-DTG amides).

In the case of BOC-DTG amides, or amides containing BOC-protecting groups on the amidic portion, the BOC-protecting groups are removed by dissolving 1 mmol of these compounds in 30 mL of anhydrous trifluoroacetic acid at room temperature and following the same procedure as described previously (e.g., Method D" for the preparation of the N$^{63}$-carboxyamides of DTG).

B'''—Preparation of the intermediate amines of compounds 46–55

1. Diamine O,O'-bis(2-aminopropil)polyethylene glycol 1900 (JEFFAMINE™ ED 2001) was purchased from (Fluka Chemie AG) (intermediate amine of compound 46)

2. For the intermediate reacting amines of compounds 47–52 a common intermediate di-(3-BOC-aminopropyl)amine

BOC—NH—(CH$_2$)$_3$—NH—(CH$_2$)$_3$—NH—BOC has been preliminarily prepared as follows:

A solution of 142 g of 2-(tert-butoxycarbonyloxy)-imino-2-phenylacetonitrile (BOC-ON, Aldrich-Chemie) in 300 mL of tetrahydrofuran (THF) is added dropwise at 10° C. to a stirred solution of 42 mL of bis-(3-aminopropyl)amine (Fluka Chemie AG) in 400 mL of THF. After hours at room temperature, the solvent is evaporated and the oily residue is dissolved in 1 liter of ethyl acetate. The resulting solution is washed with 1N NaOH (200 mL), and then with water (2×300 mL); afterwards it is extracted with 0.01N HCl (2×300 mL). The aqueous phase is adjusted at pH 8 with 1N NaOH and extracted with 500 mL of n-butanol. The organic layer is separated, washed with 250 mL of water, and then it is concentrated to a final volume of about 70 mL. On standing at 6° C. overnight crystals form which are collected by filtration, to give 75 g of pure title compound, as the free base.

$^1$H NMR: 2.93, 2.44, 1.47 (CH$_2$); 1.38 (N-BOC) 6.68 (NH).

3. N',N"-di-t-BOC-Tris-(3-aminopropyl)amine (for derivatives 47–50):

To a stirred solution of 45 g of the above di-t-BOC intermediate triamine in 500 mL of absolute ethanol, 21 mL of 3-bromo-propionitrile and 25 g of potassium carbonate are added at room temperature. The reaction mixture is stirred overnight, then it is filtered and concentrated to a final volume of about 100 mL, afterwards it is diluted with 800 mL of water. The resulting solution (pH 8) is extracted with ethyl acetate (2×800 mL). The organic layer is separated and washed with water (2×200 mL), afterwards it is concentrated to a final volume of about 100 mL. On standing at 6° C. overnight, a crystalline solid separates which is collected by filtration, yielding 34 g of di-(3 -t-BOC-aminopropyl)amino-1-propionitrile.

$^1$H NMR: 2.94, 2.63, 2.54, 2.37, 1.47 (CH$_2$); 1.36 (N-BOC); 6.73 (NH).

This product is dissolved in 200 mL of an ethanolic solution containing 8.5 g of NaOH. To the resulting solution, 4 g of Raney nickel, active catalyst (Aldrich-Chemie), is added and the suspension is hydrogenated at 2.5 arm for 10 hours. The catalyst is filtered off and the solvent is evaporated. The oily residue is dissolved in 500 mL of ethyl acetate and the resulting solution is washed with water (2×100 mL), afterwards the organic solvent is evaporated to give about 34 g of the title compound.

$^1$H NMR: 2.93, 2.54, 2.32, 1.49 (CH$_2$), 1.41 (N-BOC); 6.77 (NH).

4. 3-(3-aminopropyl) -3-(3,3 -dimethylaminopropyl)-amino-1-propylamine (for derivative 51):

To a stirred solution of 19 g of 3,3 -dimethylamino-1-propyl chloride, hydrochloride in 400 mL of absolute ethanol, 20 g of the di-t-BOC intermediate triamine and 28 g of potassium carbonate are added at room temperature followed by 3 g of potassium iodide. The reaction mixture is refluxed for 6 hours, then it is filtered, and the solvent is evaporated. The residue is re-dissolved in 400 mL of water and the resulting solution is extracted with 600 mL of ethyl acetate. The organic layer is separated, washed with water (2×200 mL), and then the solvent is evaporated, yielding an oily residue (8.7 g), the di-t-BOC derivative of the title compound, enough pure for the next step.

$^1$H NMR: 2.91, 2.42, 2.31, 2.16, 1.47 (CH$_2$), 1.36 (N-BOC), 2.09 (NCH$_3$).

A solution of this product in 30 mL of methylene chloride is treated with 30 mL of dry trifluoroacetic acid at room temperature for 2 hours, afterwards the solvents are evaporated. The oily residue is dissolved in 40 mL of absolute ethanol and dry HCl is bubbled at room temperature until complete precipitation of the product is observed. After filtration, 3.8 g of the title compound are obtained, as the tetra-hydrochloride.

$^1$H NMR: 3.2–2.91 (6-CH$_2$); 2.13–1.90 (3-CH$_2$); 2.73 (NCH$_3$).

For the condensation with BOC-DTG, the free base is used which is prepared by dissolving the tetra-hydrochloride (10 mmol) in 1N NaOH (40 mL), followed by evaporation of the resulting solution to dryness. The residue is then suspended in methylene chloride (100 mL) and the insoluble matter is filtered off. The solvent is evaporated and the oily residue is used as such without further purification.

5. 3-(3-aminopropyl)-3-(2,2 -diethylaminoethyl)-amino-1-propylamine (for derivative 52):

By following exactly the same procedure as that described above, but using 2,2-diethylamino-1-ethyl chloride, hydrochloride (21 g) for the reaction with the di-t-BOC intermediate trimmine (20 g, 11 g of the di-t-BOC derivative of the title compound are first obtained. The protecting groups are then removed analogously by treatment with trifluoroacetic acid in methylene chloride solution. The free base (as oil) is finally obtained as descrived above, yielding the title compound (8.2 g).

$^1$H NMR: 2.6–2.3 (8-CH$_2$); 1.42 (2-CH$_2$); 0.92 (2-CH$_3$).

The course of these reactions and the homogeneity of the final polyamines are checked by TLC on silica gel 60 F$_{254}$ pre-coated plates (Merck Co.), using a methylene chloride/methanol 9:1 (v/v) mixture containing 1% ammonium hydroxide as the mobile phase. The spots are developed with iodine.

6. 4-(3,3-dimethylaminopropyl) piperazine (for derivative 53):

To a stirred solution of 15.8 g of 3,3 -dimethylamino-1-propyl chloride in 300 mL of absolute ethanol, 9 mL of 1-benzyl-piperazine and 14 g of potassium carbonate are added. The reaction mixture is stirred under reflux for 6 hours, afterwards it is cooled at room temperature and filtered. Solvent is evaporated and the oily residue is dissolved in 300 mL of water. The resulting solution is extracted with methylene chloride (2×200 mL). The organic layer is separated, washed with 200 mL of water and then solvent is evaporated. The oily residue (9 g) is dissolved in 300 mL of 95% ethanol and hydrogenated (25° C., 1 atm) over 3 g of 10% Pd/C. About 1 L of H$_2$ is absorbed within 6 hours. The catalyst is filtered off and dry HCl is bubbled into the clear filtrate. A solid separated which is collected, washed with absolute ethanol and dried in vacuo at room temperature overnight, to give 7 g of pure title compound, as tri-hydrochloride.

$^1$H NMR: 2.79, 2.53, 2.30 (CH$_2$-piperazine) 2.79, 2.23, 2.15 (CH$_2$ dimethylaminopropyl); 2.10 (NCH$_3$).

The free base is obtained by dissolving this tri-hydrochloride (6 g) in 2N NaOH (30 mL) followed by extraction with methylene chloride (170 mL) and evaporation of the organic solvent. The resulting oily residue is used without further purification in the preparation of compound 53.

7. N,N'-Bis(3-aminopropyl)nonane-1,5-diamine and N,N'-Bis(3-aminopropyl)decane-1,5-diamine These derivatives are known compounds and are prepared according to the method of Israel, M. J., Rosenfield S. S., Modest, E. J., *J. Med. Chem.* 1964, 7, 710 by mono- and dy-cyanoethylation of the appropriate alpha-,omega-alkylenediamines, followed by catalytic reduction of the nitriles under unsually mild conditions.

For compounds prepared according to the procedure of A."' (46–55), see Table VII.

TABLE VII

TGA and DTG carboxyamide derivatives

| Comp. No. | Teicoplanin staring material | Amine |
|---|---|---|
| 46 | TGAC$_2$ | NH$_2$—(CH)(CH$_3$)CH$_2$[OCH$_2$CH$_2$]$_{42}$OCH$_2$CH(CH$_3$)NH$_2$ |
| 47 | TGAC$_{1-5}$ | NH$_2$(CH$_2$)$_3$—N[(CH$_2$)$_3$NH—BOC]$_2$ |
| 48 | TGAC$_{2-5}$ | NH$_2$(CH$_2$)$_3$—N[(CH$_2$)$_3$NH—BOC]$_2$ |
| 49 | TGAC$_2$ | NH$_2$(CH$_2$)$_3$—N[(CH$_2$)$_3$NH—BOC]$_2$ |
| 50 | DTG | NH$_2$(CH$_2$)$_3$—N[(CH$_2$)$_3$NH—BOC]$_2$ |

TABLE VII-continued

TGA and DTG carboxyamide derivatives

| | | |
|---|---|---|
| 51 | DTG | $NH_2(CH_2)_3-N[(CH_2)_3NH_2]-(CH_2)_3N(CH_3)_2$ |
| 52 | DTG | $NH_2(CH_2)_3-N[(CH_2)_3NH_2]-(CH_2)_2N(C_2H_5)_2$ |
| 53 | DTG | 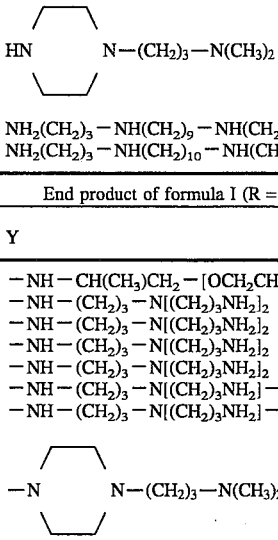 HN⟨piperazine⟩N—$(CH_2)_3$—$N(CH_3)_2$ |
| 54 | DTG | $NH_2(CH_2)_3-NH(CH_2)_9-NH(CH_2)_3NH_2$ |
| 55 | DTG | $NH_2(CH_2)_3-NH(CH_2)_{10}-NH(CH_2)_3NH_2$ |

| Comp. No. | A/AC | B | M | Y (End product of formula I (R = H)) |
|---|---|---|---|---|
| 46 | $AC_2$ | AcGlu | Man | $-NH-CH(CH_3)CH_2-[OCH_2CH_2]_{42}O-CH_2CH(CH_3)NH_2$ |
| 47 | $AC_{1-5}$ | AcGlu | Man | $-NH-(CH_2)_3-N[(CH_2)_3NH_2]_2$ |
| 48 | $AC_{2-5}$ | AcGlu | Man | $-NH-(CH_2)_3-N[(CH_2)_3NH_2]_2$ |
| 49 | $AC_2$ | AcGlu | Man | $-NH-(CH_2)_3-N[(CH_2)_3NH_2]_2$ |
| 50 | H | H | H | $-NH-(CH_2)_3-N[(CH_2)_3NH_2]_2$ |
| 51 | H | H | H | $-NH-(CH_2)_3-N[(CH_2)_3NH_2]-(CH_2)_3N(CH_3)_2$ |
| 52 | H | H | H | $-NH-(CH_2)_3-N[(CH_2)_3NH_2]-(CH_2)_2N(C_2H_5)_2$ |
| 53 | H | H | H | $-N$⟨piperazine⟩$N-(CH_2)_3-N(CH_3)_2$ |
| 54 | H | H | H | $-NH-(CH_2)_3-NH(CH_2)_9-NH(CH_2)_3NH_2$ |
| 55 | H | H | H | $-NH-(CH_2)_3-NH(CH_2)_{10}-NH(CH_2)_3NH_2$ |

HPLC Analysis is carried out with a VARIAN mod. 5000 LC pump equipped with a 20 microliter loop injector RHEODYNE mod. 7125 and a UV detector at 254 nm.

Columns: pre-column (1.9 cm.) HIBAR LICHRO CART 25–4 (Merck) pre-packed with LICHROSORB RP-8 (20–30 micrometer) followed by a column HIBAR RT 250–4 (Merck) pre-packed with LICHROSORB RP-8 (10 micrometer).

Eluents: A, 0.2% aq. $HCOONH_4$; B, $CH_3CN$.

Flow rate: 2 mL/min.

Injection: 20 microliter.

Elution: linear gradient from 20 to 60% of B in A in 30 min. The retention times of some representative compounds are reported in TABLE VIII.

Acid-Base Titrations. The products are dissolved in MCS (methylcellosolve):$H_2O$ 4:1 v/v, then an excess of 0.01M HCl in the same solvent mixture is added and the resulting solutions are titrated with 0.01N NaOH. Equivalent weight of some representative compounds are reported in TABLE IX.

$^1$H-NMR spectra at 500 MHZ are recorded in the temperature range from 20° C. to 30° C. on a BRUKER AM 500 spectrometra in DMSO-$D_6$ with tetramethylsilane (TMS) as the internal reference (delta=0.00 ppm). Table X reports the most significant chemical shift (delta ppm) of some representative compounds.

TABLE VII

Retention times ($t_R$) determined as described above for some representative compounds of the invention

| Compound No. | $t_R$ (min) |
|---|---|
| 2 | 15.6 |
| 3 | 16.1 |
| 4 | 16.1 |
| 6 | 15.7 |
| 7 | 16.9 |
| 8 | 16.8 |
| 9 | 16.9 |
| 10 | 17.1 |
| 11 | 17.1 |
| 14 | 15.7 |
| 15 | 17.0 |
| 21 | 12.4 |
| 22 | 12.7 |
| 23 | 12.8 |
| 24 | 15.8 |
| 25 | 15.7 |
| 26 | 15.7 |
| 27 | 15.9 |
| 29 | 12.5 |
| 30 | 15.9 |
| 31 | 13.6 |
| 33 | 15.4 |
| 34 | 14.4 |
| 35 | 13.8 |
| 36 | 13.4 |
| 39 | 13.1 |
| 41 | 11.0 |
| 44 | 14.2 |
| 46 | 6.7 |
| 47 | 14.4 |
| 50 | 13.6 |
| 51 | 13.9 |
| 52 | 14.2 |
| 53 | 13.1 |
| 54 | 19.5 |
| 55 | 21.0 |

TABLE IX

Yields and equivalent weight (EW) of some representative compounds of formula I. Between brackets are indicated the number of equivalents titrated for each molecule.

| Compound No. | Yield % | EW |
| --- | --- | --- |
| 2 | 72 | 675 (x3) |
| 3 | 61 | 690 (x3) |
| 4 | 59 | 681 (x3) |
| 6 | 67 | 681 (x3) |
| 7 | 81 | 506 (x4) |
| 8 | 78 | 511 (x4) |
| 9 | 81 | 512 (x4) |
| 10 | 75 | 510 (x4) |
| 11 | 70 | 504 (x4) |
| 14 | 86 | 492 (x4) |
| 15 | 81 | 496 (x4) |
| 21 | 81 | 441 (x3) |
| 22 | 63 | 442 (x3) |
| 23 | 86 | 456 (x3) |
| 24 | 84 | 348 (x4) |
| 25 | 83 | 349 (x4) |
| 26 | 86 | 361 (x4) |
| 27 | 81 | 351 (x4) |
| 29 | 88 | 369 (x4) |
| 30 | 83 | 349 (x4) |
| 39 | 96 | 421 (x4) |
| 41 | 91 | 408 (x4) |
| 44 | 83 | 386 (x4) |
| 46 | 28 | 1910 (x2) |
| 47 | 61 | 499 (x4) |
| 48 | 60 | 486 (x4) |
| 49 | 66 | 487 (x4) |
| 50 | 46 | 356 (x4) |
| 51 | 34 | 363 (x4) |
| 52 | 39 | 350 (x4) |
| 53 | 56 | 475 (x3) |
| 54 | 55 | 360 (x4) |
| 55 | 51 | 355 (x4) |

TABLE X

Significant $^1$H-NMR assingments of some representative compounds recorded in DMSO-$d_6$ with tetramethylsilane as internal reference (delta = 0.00 ppm).

| Compound | Assignments |
| --- | --- |
| Compound 2 | 3.61, 2.95 (CH$_2$-side chain); 0.83, 1.18, 1.46, 2.02 (acyl chain); 4.18–5.62 (peptidic CH's); 1.89 (acetylglucosamine); 6.18–8.45 (aromatic protons and peptidic NH's) |
| Compound 4 | 3.45, 2.82, 2.63, 2.08, 1.66 (CH$_2$-side chain); 0.87, 1.23, 1.45, 2.01 (acyl chain); 1.88 (acetylglucosamine); 4.15–5.71 (peptide CH's); 6.26–8.56 (aromatic protons and peptidic NH's) |
| Compound 6 | 3.52, 2.73, 2.58, 1.91, 1.56 (CH$_2$-side chain); 0.84, 1.15, 1.46, 2.02 (acyl chain); 1.82 (acetylglucosamine); 3.42 (mannose); 4.15–5.69 (peptidic CH's); 6.29–8.53 (aromatic protons and peptidic NH's) |
| Compound 7 | 3.68, 3.12, 2.98, 2.05 (CH$_2$-side chain); 0.84, 1.16, 1.44, 2.01 (acyl chain); 1.89 (acetylglucosamine); 3.42 (mannose); 4.13–5.58 (peptidic CH's); 6.21–8.53 (aromatic protons and peptidic NH's) |
| Compound 8 | 3.68, 2.92, 1.98 (CH$_2$-side chain); 0.82, 1.25, 1.43, 2.01 (acyl chain); 1.87 (acetylglucosamine); 4.17–5.65 (peptidic CH's); 6.26–8.57 (aromatic protons and peptidic NH's) |
| Compound 9 | 3.48, 2.98, 1.98 (CH$_2$-side chain); 0.82, 1.12, 1.43, 2.01 (acyl chain); 1.86 (acetylglucosamine); 4.16–5.62 (peptidic CH's); 6.18–8.58 (aromatic protons and peptidic NH's) |
| Compound 11 | 3.71, 2.93, 1.98, 1.73 (CH$_2$-side chain); 0.83, 1.23, 1.47, 2.02 (acyl chain); 1.89 (acetylglucosamine); 4.13–5.58 (peptidic CH's); 6.21–8.62 (aromatic protons and peptidic NH's) |
| Compound 15 | 3.52, 3.13 (CH$_2$ piperazine); 3.42–2.07 (CH$_2$-side chain); 0.83, 1.16, 1.45, 2.02 (acyl chain); 1.88 (acetylglucosamine); 4.16–5.32 (peptidic CH's); 6.18–8.53 (aromatic protons and peptidic NH's) |
| Compound 21 | 3.52, 3.04, 2.81 (CH$_2$—N); 4.15–5.62 (peptidic CH's); 6.18–8.62 (aromatic protons, peptidic NH's) |
| Compound 22 | 3.17, 2.93, 2.83, 1.87, 1.80 (CH$_2$-side chain); 4.15–5.61 (peptidic CH's); 6.18–8.53 (aromatic protons and peptidic NH's) |
| Compound 23 | 3.42, 2.98–2.71, 1.72, 1.61 (CH$_2$ spermidine); 4.15–5.63 (peptidic CH's), 6.19–8.43 (aromatic protons and peptidic NH's) |
| Compound 24 | 3.38, 3.12, 2.98 (CH$_2$—N), 1.89 (CH$_2$); 4.17–5.58 (peptidic CH's); 6.18–8.48 (aromatic protons, peptidic NH's) |
| Compound 25 | 3.34, 3.08, 2.84, 1.78 (CH$_2$-side chain); 4.16–5.58 (peptidic CH's); 8.31–8.48 (aromatic protons and peptidic NH's) |
| Compound 26 | 3.36, 2.98, 2.87 (CH$_2$—N); 1.89, 1.77 (CH$_2$); 4.15–5.62 (peptidic CH's); 6.18–8.42 (aromatic protons, peptidic NH's) |
| Compound 27 | 3.12, 3.03–2.82, 1.88, 1.81, 1.65 (CH$_2$-side chain); 4.15–5.62 (peptidic CH's); 6.19–8.41 (aromatic protons and peptidic NH's) |
| Compound 29 | 3.48, 3.12, 2.83, 2.64 (CH$_2$—N); 4.18–5.61 (peptidic CH's); 6.21–8.70 (aromatic protons and peptidic NH's) |
| Compound 30 | 3.49, 3.11, 2.95, 2.85, 1.85 (CH$_2$ side chain); 4.18–5.81 (peptidic CH's); 6.21–8.56 (aromatic protons, peptidic NH's) |
| Compound 39 | 3.71, 3.37, 2.98, 1.98, 1.82 (spermine); 1.86 (acetylglucosamine); 3.44 (mannose); 4.16–5.58 (peptidic CH's); 6.29–8.54 (aromatic protons and peptidic NH's). |
| Compound 46 | 3.41, 3.23, 3.16, 2.94 (CH$_2$-side chain); 1.12, 1.23 (CH$_3$-side chain); 0.81, 1.15, 1.46, 2.00 (acyl chain); 1.86 (acetylglucosamine); 4.16–5.59 (peptidic CH's); 6.23–8.01 (aromatic protons, peptidic NH's). |
| Compound 47 | 3.45, 3.09, 2.35, 1.84 (CH$_2$-side chain); 0.82, 1.14, 1.46, 2.03 (acyl chain); 1.86 (acetylglucosamine); 4.12–5.62 (peptidic CH's); 6.23–8.43 (aromatic protons, peptidic NH's). |
| Compound 50 | 3.43, 3.24, 2.85, 1.84 (CH$_2$-side chain); 4.12–5.62 (peptidic CH's); 6.21–8.51 (aromatic protons, peptidic NH's). |
| Compound 51 | 3.45, 3.39, 3.05, 2.91, 2.12, 1.98 (CH$_2$-side chain); 2.74 (NCH$_3$); 4.13–5.59 (peptidic CH's); 6.18–8.61 (aromatic protons, peptidic NH's). |
| Compound 52 | 3.48, 3.12, 1.89 (CH$_2$-side chain); 1.18 (2CH$_3$-ethyl)l 4.12–5.61 (peptidic CH's); 6.20–8.52 (aromatic protons, peptidic NH's). |
| Compound 53 | 3.42, 3.39, 3.30, 1.98 (CH$_2$-pip., CH$_2$-propyl); 2.75 (NCH$_3$); 4.05–5.63 (peptidic CH's); 6.32–8.52 (aromatic protons, peptidic NH's). |
| Compound 55 | 3.32, 2.98, 2.76, 1.86, 1.52, 1.24 (CH$_2$-side chain); 4.13–5.62 (peptidic CH's); 6.31–8.42 (aromatic protons, |

TABLE X-continued

Significant ¹H-NMR assingments of some representative compounds recorded in DMSO-$d_6$ with tetramethylsilane as internal reference (delta = 0.00 ppm).

| Compound 54 | peptidic NH's). 3.37, 3.34, 3.07, 2.86, 2.78, 1.75, 1.59, 1.26 ($CH_2$-side chain); 4.14–5.61 (peptidic CH's); 6.21–8.34 (aromatic protons, peptidic NH's). |
|---|---|

We claim:

1. A teicoplanin amide derivative of formula I

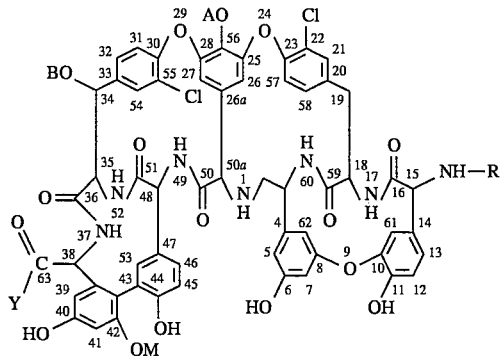

wherein

R represents hydrogen or a protecting group of the amine function;

Y represents a compound of formula

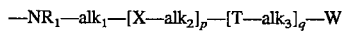

wherein $R_1$ represents hydrogen or ($C_1$-$C_4$)alkyl;

$alk_1$, $alk_2$ and $alk_3$ each independently represents a linear or branched alkylene of 2 to 10 carbon atoms;

p represents an integer ranging from 1 to 50;

q represents an integer ranging from 0 to 12;

X represents a —$NR_2$— group or an oxygen atom wherein $R_2$ represents hydrogen, ($C_1$-$C_4$)alkyl, a group $alk_4NR_3R_4$ wherein $alk_4$ represents a linear or branched alkylene of 2 to 4 atoms, $R_3$ is hydrogen or ($C_1$-$C_4$)alkyl and $R_4$ is hydrogen, ($C_1$-$C_4$)alkyl or a 5–6 membered cycloalkyl; or $R_1$ and $R_2$ taken together represent a ($C_2$-$C_4$)alkylene moiety connecting the two nitrogen atoms with the proviso that in such case p is 1;

T represents a —$NR_5$— group or an oxygen atom wherein $R_5$ is hydrogen, ($C_1$-$C_4$)alkyl, a group $alk_5NR_6R_7$ wherein $alk_5$ represents a linear or branched alkylene of 2 to 4 atoms, $R_6$ is hydrogen or ($C_1$-$C_4$)alkyl and $R_7$ is hydrogen, ($C_1$-$C_4$)alkyl or a 5–6 membered cycloalkyl; or $R_2$ and $R_5$ taken together represent a ($C_2$-$C_4$)alkylene moiety connecting the two nitrogen atoms with the proviso that in such case both p and q are 1;

W represents hydroxy, $NR_8R_9$ or $N^{\oplus}R_{11}R_{12}R_{13}An^{\ominus}$, $R_8$ represents hydrogen or ($C_1$-$C_6$)alkyl, $R_9$ represents hydrogen, ($C_1$-$C_6$)alkyl, ($C_5$-$C_6$)cycloalkyl or $COOR_{10}$, $R_{10}$ represents ($C_1$-$C_6$)acyloxy($C_1$-$C_4$)alkyl, and, $R_{11}$, $R_{12}$, and $R_{13}$ each independently represents ($C_1$-$C_4$)alkyl and $An^{\ominus}$ is an anion derived from a pharmaceutically acceptable acid; with the proviso that when simultaneously X is $NR_2$, p is 1 and q is zero, then W is not represented by hydroxy;

A represents H or —N[($C_9$-$C_{12}$)aliphatic acyl]- beta-D-2-deoxy-2-aminoglucopyranosyl, B represents hydrogen or N-acetyl-beta-D-2-deoxy-2-aminoglucopyranosyl;

M represents hydrogen or alpha-D-mannopyranosyl or the pharmaceutically addition salt thereof;

with the further proviso that B represents hydrogen only when A and M are simultaneously hydrogen (SEQ ID NO 1).

2. A compound of claim 1 wherein the ($C_9$-$C_{12}$) aliphatic acyl radicals of the symbol A is one of the following:

(Z)-4-decenoyl, 8-methylnonanoyl, decanoyl, 8-methyldecanoyl, 9-methyldecanoyl, 6-methyloctanoyl, nonanoyl, 10-methylundecanoyl and dodecanoyl.

3. A compound of claim 1 wherein X represents —$NR_2$— and T represents —$NR_5$—; $alk_1$, $alk_2$, and $alk_3$, each represent a ($C_2$-$C_{10}$) linear chain, p is an integer from 1 to 5, and q is an integer from 0_ to 12.

4. A compound of claim 1 wherein both X and T represent oxygen atoms and p and q are such that the sum of p+q represent an integer from 2 to 50.

5. A compound of claim 1 wherein X represents —NR$_2$— wherein R$_2$ is hydrogen, a (C$_1$–C$_4$)alkyl or a group alk$_4$NR$_3$R$_4$ wherein alk$_4$, R$_3$ and R$_4$ are defined as in claim 1.

6. A compound of claim 1 wherein p is 1 and X is —NR$_2$— wherein R$_2$ taken together with R$_1$ represent a (C$_2$–C$_3$)alkylene moiety connecting the nitrogen atoms.

7. A compound of claim 1 wherein p is 1, q is 1 and X and T are —NR$_2$— and —NR$_5$— respectively, wherein R$_2$ and R$_5$ taken together represent a (C$_2$–C$_3$)alkylene moiety connecting the nitrogen atoms.

8. A compound of claim 6 wherein the alkylene moiety is a group —CH$_2$—CH$_2$—.

9. A compound of claim 1 wherein X and T are oxygen atoms and W is hydroxy or —NR$_8$R$_9$— wherein R$_8$ is hydrogen or (C$_1$–C$_4$)alkyl and R$_9$ is hydrogen, (C$_1$–C$_4$)alkyl, cyclopentyl or cyclohexyl.

10. A compound of claim 1 wherein W represents —NR$_8$R$_9$— wherein R$_8$ is as defined and R$_9$ is COOR$_{10}$ in which R$_{10}$ is a (C$_1$–C$_6$)acyloxy-(C$_1$–C$_4$)alkyl group.

11. A compound of claim 10 wherein the (C$_1$–C$_4$)alkyl group of the (C$_1$–C$_6$)acyloxy-(C$_1$–C$_4$)alkyl moiety is a methylene optionally substituted with a (C$_1$–C$_3$)linear or branched alkyl chain.

12. A compound according to claim 1 in which R is represented by hydrogen; A is represented by hydrogen; B is represented by hydrogen; M is represented by hydrogen and Y is represented by —NH—(CH$_2$)$_3$—N[(CH$_2$)$_3$—NH$_2$]$_2$.

13. A compound according to claim 1 in which R is represented by hydrogen; A is represented by hydrogen; B is represented by hydrogen; M is represented by hydrogen; and Y is represented by —NH(CH$_2$)$_3$—NH(CH$_2$)$_3$—NH(CH$_2$)$_3$—NH$_2$.

14. An antibacterial formulation comprising a compound according to claim 1 present in an antibacterially effective amount in admixture with a pharmaceutically acceptable carrier.

15. An antibacterial formulation comprising a compound according to claim 12 present in an antibacterially effective amount in admixture with a pharmaceutically acceptable carrier.

16. An antibacterial formulation comprising a compound according to claim 13 present in an antibacterially effective amount in admixture with a pharmaceutically acceptable carrier.

17. A method for the treatment of bacterial infections comprising administering to a patient in need thereof an antibacterially effective amount of a compound according to claim 1.

18. A method for the treatment of bacterial infections comprising administering to a patient in need thereof an antibacterially effective amount of a compound according to claim 12.

19. A method for the treatment of bacterial infections comprising administering to a patient in need thereof an antibacterially effective amount of a compound according to claim 13.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Xaa  Xaa  Xaa  Xaa  Xaa  Xaa  Xaa
1                 5
```